(12) United States Patent
Roseman et al.

(10) Patent No.: US 9,267,141 B2
(45) Date of Patent: Feb. 23, 2016

(54) CONVERSION OF CHITIN INTO N-ACETYLGLUCOSAMINE, GLUCOSAMINE AND BIOETHANOL

(75) Inventors: Saul Roseman, Pikesville, MD (US); Dorinda A. Gershman, legal representative, Cleveland Heights, OH (US); Xibing Li, Phoenix, MD (US); Donald Comb, Manchester, MA (US)

(73) Assignees: The Johns Hopkins University, Baltimore, MD (US); New England Biolabs, Ipswich, MA (US)

( * ) Notice: Subject to any disclaimer, the term of this patent is extended or adjusted under 35 U.S.C. 154(b) by 912 days.

(21) Appl. No.: 13/264,273

(22) PCT Filed: Apr. 16, 2010

(86) PCT No.: PCT/US2010/031504
§ 371 (c)(1),
(2), (4) Date: Sep. 27, 2012

(87) PCT Pub. No.: WO2010/123784
PCT Pub. Date: Oct. 28, 2010

(65) Prior Publication Data
US 2012/0142058 A1    Jun. 7, 2012

Related U.S. Application Data

(60) Provisional application No. 61/172,251, filed on Apr. 24, 2009.

(51) Int. Cl.
| | | |
|---|---|---|
| *C12N 1/20* | (2006.01) | |
| *C12P 19/26* | (2006.01) | |
| *C12P 39/00* | (2006.01) | |
| *C12P 7/08* | (2006.01) | |
| *C12N 15/52* | (2006.01) | |

(52) U.S. Cl.
CPC . *C12N 15/52* (2013.01); *C12P 7/08* (2013.01); *C12P 19/26* (2013.01); *C12P 39/00* (2013.01); *Y02E 50/17* (2013.01)

(58) Field of Classification Search
USPC .............................................. 435/252.3, 84
See application file for complete search history.

(56) References Cited

U.S. PATENT DOCUMENTS 6,372,457 B1    4/2002  Berry et al.
8,734,814 B2 *  5/2014  Datta et al. ................. 424/261.1

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sousa et al., Microbiology 148(Pt5):1291-1303, 2002.*
Zhou et al., Cell Mol Life Sci 63(19-20):2260-2290, 2006.*
Kozak, M., Gene 234:187-208, 1999.*
Enos-Berlage et al., Molecular Microbiology 55(4):1160-1182, 2005.*
Kadokura et al., Applied Microbiology and Biotechnology 75:357-365, 2007.*
Li et al., PNAS 101(2):627-631, 2004.*
Bassler et al., Journal of Biological Chemistry 266(36):24276-24286, 1991.*
Deng MD et al., "Metabolic engineering of *Escherichia coli* for industrial production of glucosamine and N-acetylglucosamine", Metabolic Engineering (2005) vol. 7, No. 3, pp. 201-214.
Deng MD et al., "Engineering a new pathway for N-acetylglucosamine production: coupling a catabolic enzyme, glucosamine-6-phosphate deaminase, with a biosynthetic enzyme, glucosamine-6-phosphate N-acetyltransferase", Enzyme and Microbial Technology (2006) vol. 38, No. 4, pp. 828-834.
Meibom KL et al., "The Vibrio cholerae chitin utilization program", Proceedings of the National Academy of Sciences, (2004) vol. 101, No. 8, pp. 2524-2529.
Toratani T et al., "The importance of chitobiase and N-acetylglucosamine (GlcNAc) uptake in N,N'-diacetylchitobiose [(GlcNAc)2] utilization by Serratia marcescens 2170", (2008) Microbiology, vol. 154, pp. 1326-1332.

* cited by examiner

*Primary Examiner* — Delia Ramirez
(74) *Attorney, Agent, or Firm* — Johns Hopkins Technology Transfer

(57) ABSTRACT

Compositions and methods are provided for converting chitin into N-acetylglucosamine, glucosamine and ethanol. The chitin may be used directly from the environment, for example, as occurs in invertebrate cuticles, fungal cells and/or algae. Mutant bacteria were created by knocking out or inactivating one or more genes preferably resulting in the chitin catabolic sensor maintaining an activated state. Methods are further provided for converting the N-acetylglucosamine into ethanol by means of a genetically engineered yeast strain which can be optionally co-cultivated with the Vibrionaceae to produce significant yields of ethanol.

20 Claims, 19 Drawing Sheets

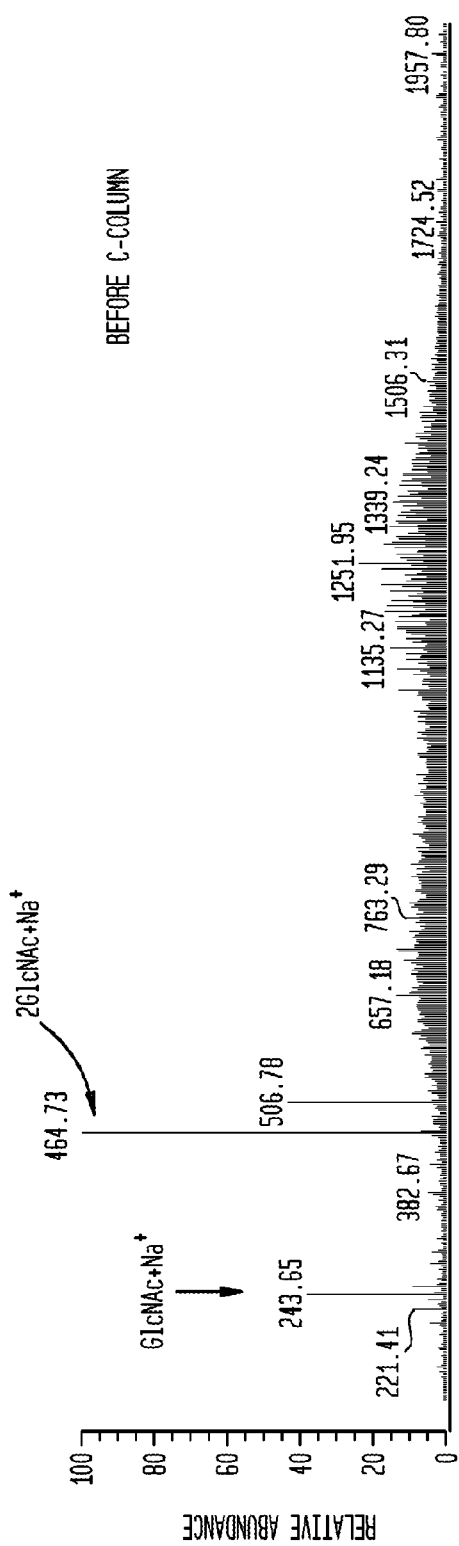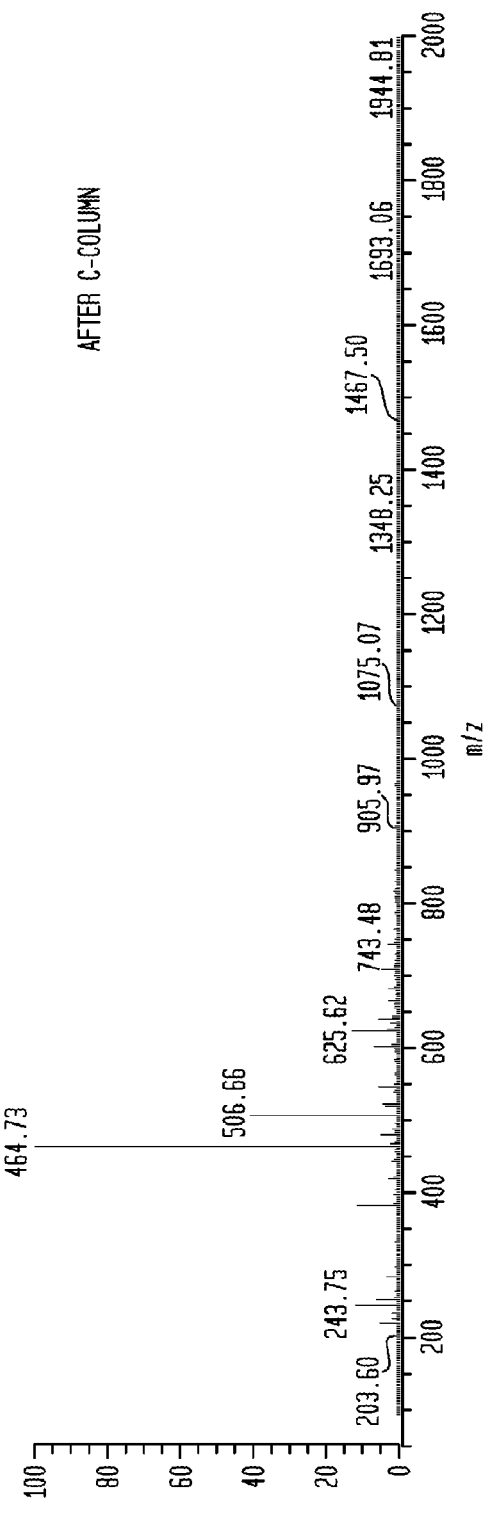
FIG. 18A / FIG. 18B

SEQUENCE LISTING

```
<160> NUMBER OF SEQ ID NOS: 16

<210> SEQ ID NO 1
<211> LENGTH: 24
<212> TYPE: DNA
<213> ORGANISM: artificial
<220> FEATURE:
<223> OTHER INFORMATION: primer

<400> SEQUENCE: 1
gcagatctcg ttggctgctt atca                                    24

<210> SEQ ID NO 2
<211> LENGTH: 28
<212> TYPE: DNA
<213> ORGANISM: artificial
<220> FEATURE:
<223> OTHER INFORMATION: primer

<400> SEQUENCE: 2
agtagctcga gatgtcagca cgcaatga                                28

<210> SEQ ID NO 3
<211> LENGTH: 28
<212> TYPE: DNA
<213> ORGANISM: artificial
<220> FEATURE:
<223> OTHER INFORMATION: primer

<400> SEQUENCE: 3
gacatctcga gctacttcgt gttccgta                                28

<210> SEQ ID NO 4
<211> LENGTH: 21
<212> TYPE: DNA
<213> ORGANISM: artificial
<220> FEATURE:
<223> OTHER INFORMATION: primer

<400> SEQUENCE: 4
ctagcttcac aactcccata g                                       21
```

```
<210> SEQ ID NO 5
<211> LENGTH: 26
<212> TYPE: DNA
<213> ORGANISM: artificial
<220> FEATURE:
<223> OTHER INFORMATION: primer

<400> SEQUENCE: 5
gcgagatcta gcagcacaag taggta                                          26

<210> SEQ ID NO 6
<211> LENGTH: 26
<212> TYPE: DNA
<213> ORGANISM: artificial
<220> FEATURE:
<223> OTHER INFORMATION: primer

<400> SEQUENCE: 6
atggctcgag gatgccaatg tactca                                          26

<210> SEQ ID NO 7
<211> LENGTH: 27
<212> TYPE: DNA
<213> ORGANISM: artificial
<220> FEATURE:
<223> OTHER INFORMATION: primer

<400> SEQUENCE: 7
gcatcctcga gccataacaa agctcag                                         27

<210> SEQ ID NO 8
<211> LENGTH: 28
<212> TYPE: DNA
<213> ORGANISM: artificial
<220> FEATURE:
<223> OTHER INFORMATION: primer

<400> SEQUENCE: 8
gcggagatct gcctttgatg ttttctgc                                        28

<210> SEQ ID NO 9
<211> LENGTH: 26
<212> TYPE: DNA
<213> ORGANISM: artificial
<220> FEATURE:
<223> OTHER INFORMATION: primer

<400> SEQUENCE: 9
ggagatctac agcactagca acagca                                          26

<210> SEQ ID NO 10
<211> LENGTH: 27
<212> TYPE: DNA
<213> ORGANISM: artificial
<220> FEATURE:
<223> OTHER INFORMATION: primer

<400> SEQUENCE: 10
cagacctcga gcgaaataca ggcgtgt                                         27

<210> SEQ ID NO 11
<211> LENGTH: 28
<212> TYPE: DNA
<213> ORGANISM: artificial
<220> FEATURE:
```

```
<223> OTHER INFORMATION: primer

<400> SEQUENCE: 11
atttcgctcg aggtctgagt tgctggat                                              28

<210> SEQ ID NO 12
<211> LENGTH: 24
<212> TYPE: DNA
<213> ORGANISM: artificial
<220> FEATURE:
<223> OTHER INFORMATION: primer

<400> SEQUENCE: 12
agatctgaag aacacgttcc gcag                                                  24

<210> SEQ ID NO 13
<211> LENGTH: 24
<212> TYPE: DNA
<213> ORGANISM: artificial
<220> FEATURE:
<223> OTHER INFORMATION: primer

<400> SEQUENCE: 13
aagatctgag tgttcggagt ccag                                                  24

<210> SEQ ID NO 14
<211> LENGTH: 28
<212> TYPE: DNA
<213> ORGANISM: artificial
<220> FEATURE:
<223> OTHER INFORMATION: primer

<400> SEQUENCE: 14
catcctctcg agtacctaag ctcgctaa                                              28

<210> SEQ ID NO 15
<211> LENGTH: 27
<212> TYPE: DNA
<213> ORGANISM: artificial
<220> FEATURE:
<223> OTHER INFORMATION: primer

<400> SEQUENCE: 15
aggtactcga gaggatgctg gtataga                                               27

<210> SEQ ID NO 16
<211> LENGTH: 26
<212> TYPE: DNA
<213> ORGANISM: artificial
<220> FEATURE:
<223> OTHER INFORMATION: primer

<400> SEQUENCE: 16
ggagatctaa ggagcgatct gctttg                                                26
```

CONVERSION OF CHITIN INTO N-ACETYLGLUCOSAMINE, GLUCOSAMINE AND BIOETHANOL

CROSS-REFERENCE TO RELATED APPLICATIONS

This application is a 35 U.S.C. §371 U.S. national entry of International Application PCT/US10/31504 having an international filing date of Apr. 16, 2010, which claims the benefit of U.S. Provisional Application No. 61/172,251, filed Apr. 24, 2009, the content of each of the aforementioned applications is herein incorporated by reference in their entirety.

INCORPORATION-BY-REFERENCE OF MATERIAL SUBMITTED ELECTRONICALLY

This application contains a sequence listing. It has been submitted electronically via EFS-Web as an ASCII text file entitled "320-PCT_20100415_gd-seq-listing_02.txt." The sequence listing is 4,096 bytes in size, and was created on Apr. 16, 2010. It is hereby incorporated by reference in its entirety.

BACKGROUND

About $10^{11}$ metric tons of chitin are produced annually in the ocean waters, $10^9$ tons from copepods alone, the most abundant animals on earth. Chitin fibrils embedded in a matrix of highly cross-linked, insoluble protein(s) make up a significant fraction of the cuticles of arthropoda, annalida, mollusca, and the cell walls of many fungi and yeasts.

Each chitin fibril molecule consists of a straight chain of over a thousand N-acetylglucosamine (GlcNAc) monomers linked by β,1-4 bonds similar to beads on a string. These fibril molecules are cross-linked via hydrogen bonds to each other, giving enormous strength to the fibers. Native chitin also contains a small percentage of glucosamine (GlcN). Harsh chemical methods (acid and alkali) are used to isolate chitin, thus yielding an increased quantity of glucosamine in the polymer.

The ecological significance of chitin degradation has been recognized for over a century. The carbon and nitrogen cycles would cease if this highly insoluble polysaccharide was not recycled in a biologically useful form. The commercial significance of chitin breakdown has also been recognized in the context of production of bioavailable sugars and in medicine for the treatment of arthritis, and other joint problems.

Although a constant rain of chitin falls to the ocean floors (marine snow), marine sediments contain only traces of the polymer. Zobell and Rittenberg (*J. Bacteriol.* 35: 275-287 (1937)) demonstrated the existence of chitinivorous bacteria that cause degradation of chitin and are ubiquitous in the marine environment.

Historically, it was thought that only two steps were required to convert chitin to GlcNAc. The first step relied on a chitinase (EC:3.2.1.14) that would yield primarily the disaccharide, (GlcNAc-β,1-4-GlcNAc, or (GlcNAc)$_2$ or N,N'-diacetylchitobiose). The second step was thought to utilize a β-N-acetylglucosaminidase (EC: 3.2.1.52) to hydrolyze the disaccharide to GlcNAc. Further investigation revealed that the chitin catabolic cascade was much more complex involving a minimum of three signaling pathways that rely on many gene products. For instance, using DNA microarray analyses (Meibom et al. *Proc. Natl. Acad. Sci. U.S.A* 101: 2524-2529 (2004)), some 200 genes have been shown to be involved in the growth of *Vibrio cholerae* on living copepods.

Traditionally, chitin is purified from invertebrate cuticles by a process that includes using dilute acid to remove the calcium from the cuticles, followed by repetitive hot strong alkali treatment, and acid extraction to remove the highly insoluble protein matrix that surrounds the chitin in the cuticles. Chitin can then be completely hydrolyzed to GlcN by refluxing it with 4N-6N HCl for 16 hours or more. The GlcN, HCl salt must then be purified, which is accomplished by fractional crystallization or ion-exchange chromatography.

Thus, the chemical isolation of GlcN as an HCl or sulfate salt is expensive and is a high energy-consuming chemical procedure presenting ecological problems associated with the disposal of large volumes of waste products. A new method of fermentation that could convert chitin into GlcNAc or GlcN on an industrial scale would facilitate the preparation of medicines and would also provide an alternative bioavailable source of sugars. Additionally, it would be valuable if these sugars could be converted to ethanol.

SUMMARY

In an embodiment of the invention, a composition is provided that includes a genetically engineered mutant bacterium in which one or more genes have been deleted or inactivated or their expression product rendered inactive, such that the mutant bacterium is capable of converting chitin to products including N-acetylglucosamine but is not capable of substantially degrading glucosamine and N-acetylglucosamine. These products are preferably released into the extracellular growth medium. In an embodiment of the invention, one or a combination of the following genes or their equivalents are deleted or inactivated. These include part or all of an: operon or combination of operons selected from NagACE operon, chitin operon including the periplasmic (GlcNAc)$_2$ binding protein, and chitibiose operon; or NagB. However, the chitin catabolic sensor (ChiS) is not inactivated. Rather, it preferably becomes constitutively activated.

An example of a mutant bacterium includes a mutant gram negative bacterium for example a mutant Vibrionaceae for example a mutant *Vibrio* species for example a mutant of *Vibrio alginolyticus* (*V. alginolyticus*), *Vibrio cholerae* (*V. cholerae*) and *Vibrio furnissii* (*V. furnissii*).

The chitin referred to throughout may be environmental chitin such as is found in invertebrates such as arthropods, mollusks and annelids; fungi; and algae. For example, chitin can be found in the cuticles or exoskeletons of invertebrates and in the mycelium and cell walls of fungi. Alternatively, the chitin may be obtained from a purified or semi-purified source.

In another embodiment of the invention, a method is provided in which the mutant bacterium described above is used to obtain products that comprise at least one of N-acetylglucosamine and glucosamine. The method includes (a) adding the mutant *Vibrio* species to an extracellular medium comprising chitin; (b) converting the chitin into products comprising N-acetylglucosamine by means of the mutant *Vibrio* species; and (c) obtaining at least one of N-acetylglucosamine and glucosamine in the extracellular medium. The N-acetylglucosamine in the extracellular medium can be purified on an activated charcoal column.

Any of the N-acetylglucosamine can be converted to glucosamine by acid hydrolysis or by means of a deacetylase.

In an additional embodiment of the invention, a method is provided for forming a mutant bacterium exemplified by a mutant gram negative bacterium exemplified by a mutant Vibrionaceae exemplified by a mutant *Vibrio* species such as mutants of *V. alginolyticus, V. cholerae,* or *V. furnissii.* The method includes (a) obtaining a bacterium from a source; (b) knocking out or inactivating one or more genes for expressing at least one protein from one or both of a signal transduction system and a chitin degradative pathway in the bacterium, exemplified by part or all of an operon or a combination of operons selected from NagACE operon, chitin operon including the periplasmic BP, but not ChiS which is preferably constitutively activated and chitobiose operon (ChB) or NagB; and (c) forming a mutant bacterium as described above.

The source of the bacterium may be the environment such as a terrestrial environment, an aqueous environment such as a marine environment; a hospital patient; or a culture collection such as provided by the ATCC.

The product of the method of forming a mutant bacterium is an organism that is capable of hydrolyzing chitin contained in a growth medium and producing N-acetylglucosamine and/or glucosamine.

In an embodiment of the invention, the glucosamine obtained by the described methods involving fermentation using chitin and mutant bacteria may be used in production of nutraceutical glucosamine for the treatment of arthritis in humans and non-human mammals.

In an additional embodiment of the invention, a method is provided in which a mutant bacterium such as described above is used in a process to make ethanol. The method includes: (a) adding the mutant bacterium to a medium that comprises chitin; (b) converting the chitin into a product that comprises comprising extracellular N-acetylglucosamine by means of the bacterium; and (c) converting the N-acetylglucosamine into ethanol by additional fermentation, for example, using genetically engineered yeast cells.

The extracellular N-acetylglucosamine can be harvested and then added to a culture of genetically engineered yeast cells so as to convert the N-acetylglucosamine into ethanol. Alternatively, genetically engineered yeast may be added to the mutant bacterium in growth medium at the end of the fermentation of chitin to products comprising N-acetylglucosamine. Alternatively, the mutant bacterium and the genetically engineered yeast can be co-cultivated to produce ethanol from chitin in a single fermentation. In one example, the mutant bacterium is *V. alginolyticus*. In another example, the genetically engineered yeast is a genetically engineered *Saccharomyces*.

A=extracellular protease(s);
B=chitinases (EC: 3.2.1.14);
BP=periplasmic $(GlcNAc)_2$ binding protein
C=general porins and a chitoporin;
D=chitodextrinase (EC: 3.2.1.14);
E=β-N-acetylglucosaminidase (EC 3.2.1.52);
F=2-component signal transduction system;
G=ABC type transporter;
H=phosphoenolpyruvate: glycose phosphotransferase system (PTS system) for GlcNAc (NagE gene product);
I=N,N'-diacetylchitobiose phosphorylase (EC: 2.4.1.-); Park et al. (2000) J. Biol. Chem. 275 p 33077-33083
J=N-acetylglucosamine ATP kinase (EC: 2.7.1.59);
K=N-acetylglucosamine-phosphate mutase (EC:5.4.2.3);
L=N-acetylglucosamine-6-phosphate deacetylase (EC: 3.5.1.25); and
M=Glucosamine-6-phosphate deaminase (EC: 3.5.99.6).

FIGS. 5A-5E show extracellular chitinase expression in *V. furnissii*, which is characteristic of *Vibrio* species capable of hydrolyzing chitin. Intact cells of *V. furnissii* were streaked out on agar medium overlayed with colloidal chitin to produce colonies. The secreted bacterial chitinases yielded clear areas resulting from hydrolysis of the chitin.

In FIGS. 5A and 5B, the agar contained rich broth resulting in rapid growth of the bacteria, but only small quantities of chitinase(s) were produced. In FIGS. 5C and 5D, a minimal synthetic medium was used with lactate as the carbon source. Wild type cells grew better in the presence of 0.5% lactate compared with 0.05% lactate, but produced less chitinase. In FIG. 5E, the clearing of a substantial area of the chitin plate was evidence that a large amount of chitinase(s) were secreted in labeled minimal medium with no carbon source except for colloidal chitin. The colonies can barely be seen in this figure.

Figure 6:
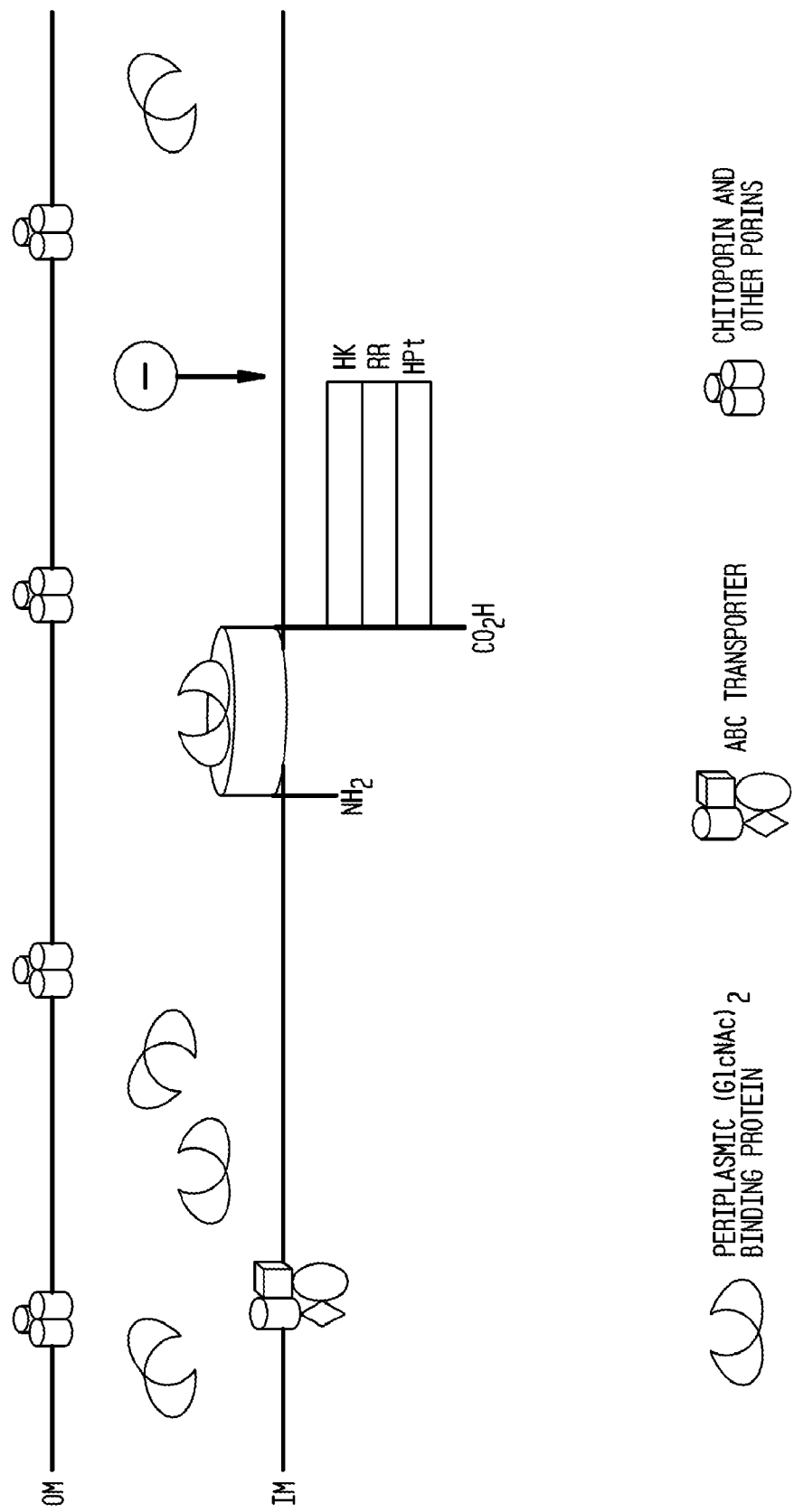

FIG. 6 shows a cartoon of the two component ChiS located partly in the periplasm and partly in the cytoplasm. Maximal expression of the chitinases and other proteins critical to chitin catabolism are obtained only when ChiS is activated. ChiS forms a chitin signal transduction system across the inner membrane (IM) of *Vibrio*. In the cartoon, the BP binds to the sensor in the periplasmic space. This results in the sensor being inactive or "OFF". The figure also contains graphic representations of (i) BP (ii) ABC transporter and (iii) chitoporin and other porins as shown in the key.

Figure 7:
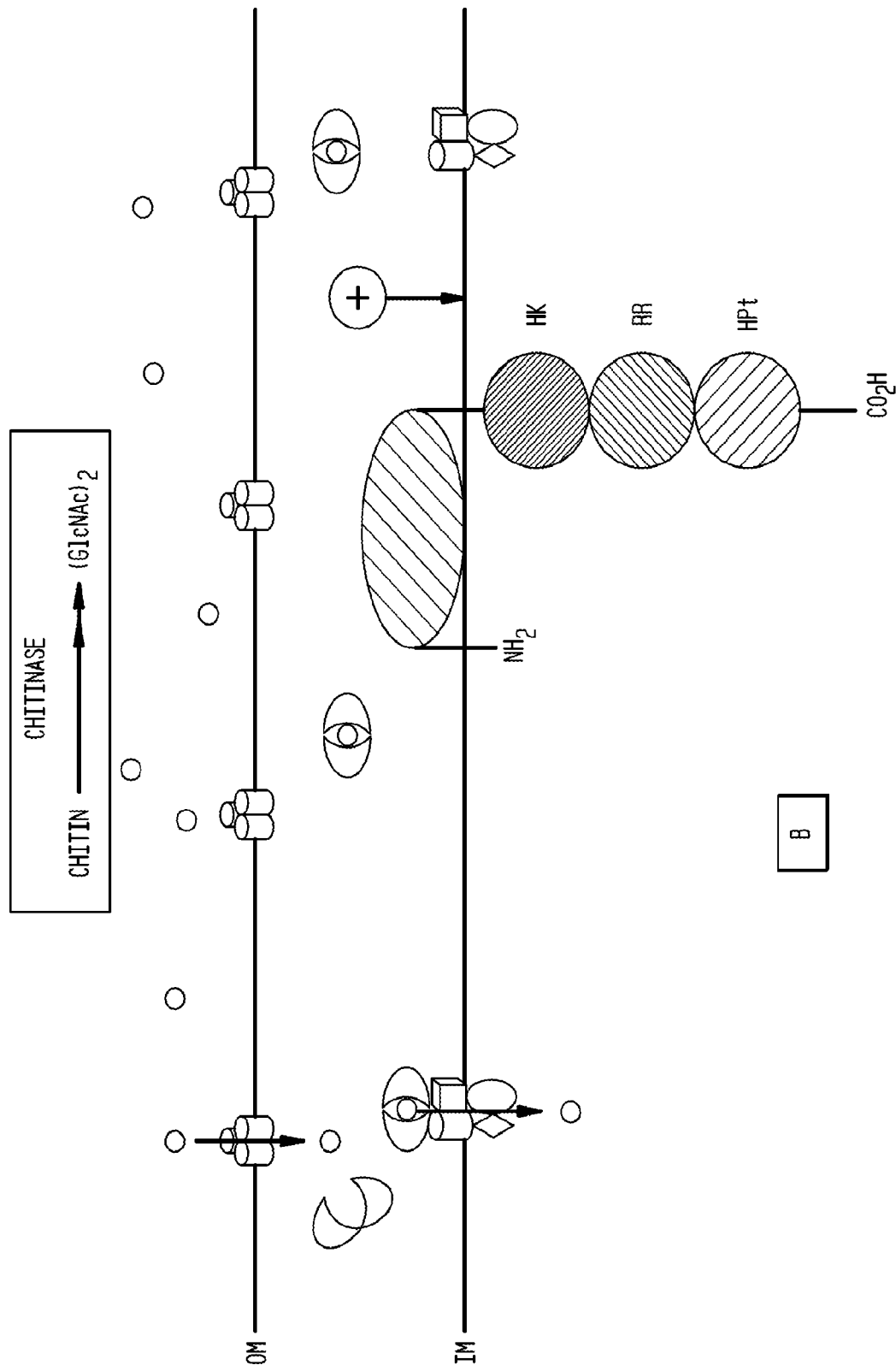

FIG. 7 shows how environmental chitin turns the sensor to the "ON" mode. A low level of chitinase(s) is secreted by the cells, reaches the chitin, and hydrolyzes it primarily to the disaccharide, $(GlcNAc)_2$, which enters the periplasmic space. Here, it competes with ChiS for the BP When BP is released from the BP/ChiS complex, ChiS assumes a different conformation, and is turned on, or active. Maximal expression of the chitinases and other critical proteins is attained in the "ON".

Figure 8:
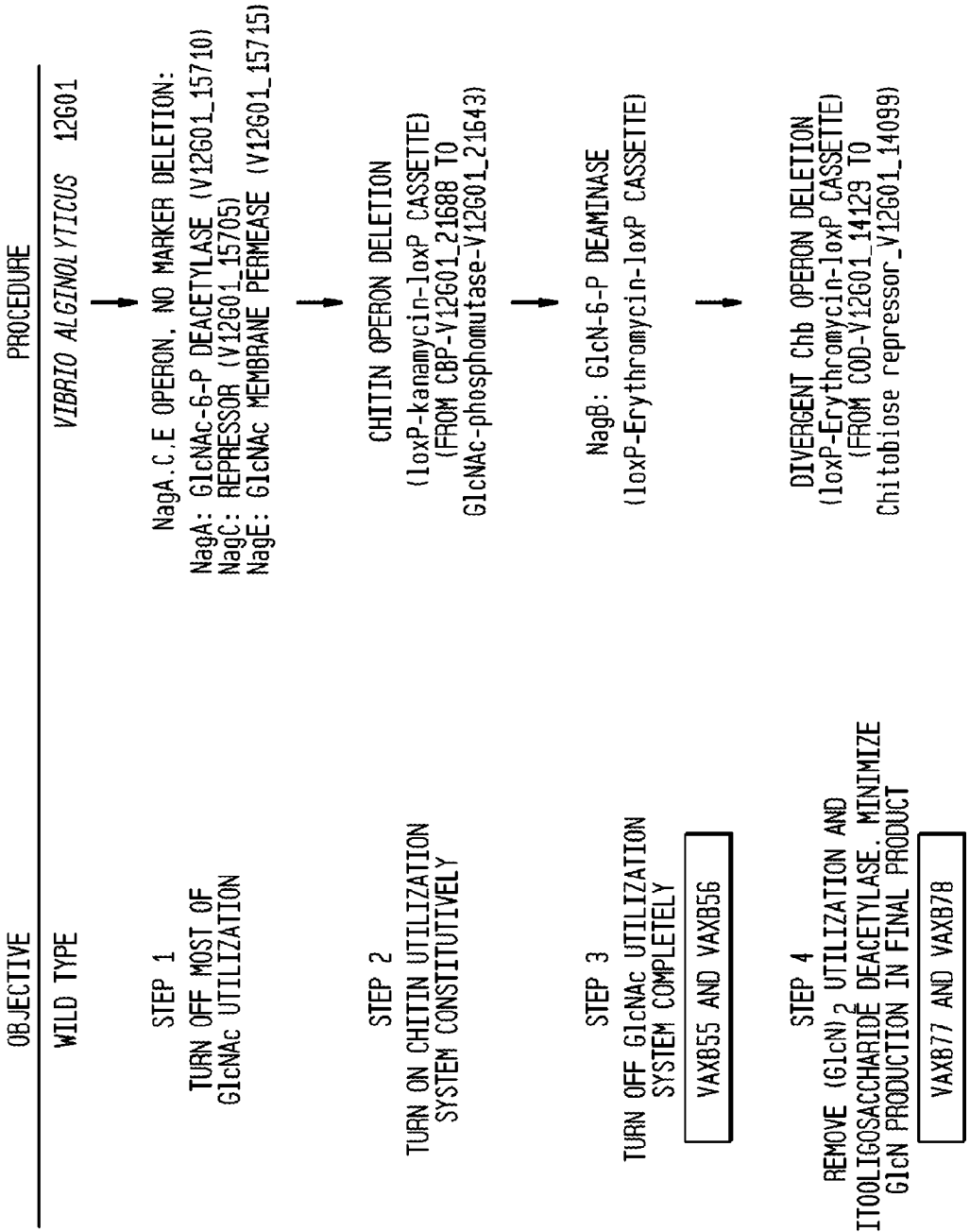

FIG. 8 shows the construction of *Vibrio alginolyticus* 12G01 mutants VAXB55 and also the mutants VAXB77 which lack the chitin oligosaccharide deacetylase. The same approach was used to construct VAXB56 and VAXB78, but the antibiotic markers were removed from VAXB55 and VAXB77, respectively, as shown in FIG. 10.

(1) Turn off GlcNAc utilization at least 90% by deleting the NagA,C,E operon
(2) Turn on chitin utilization constitutively by deleting the chitin operon, including the periplasmic (GlcNAc)$_2$ binding protein BP, but not the sensor ChiS. Turn off GlcNAc utilization completely by deleting NagB, GlcN-6-P deaminase
(3) Remove disaccharide utilization, [(GlcNAc)$_2$ and (GlcN)$_2$], and chitooligosaccharide deacetylase, thereby minimizing GlcN production.

Figure 9:
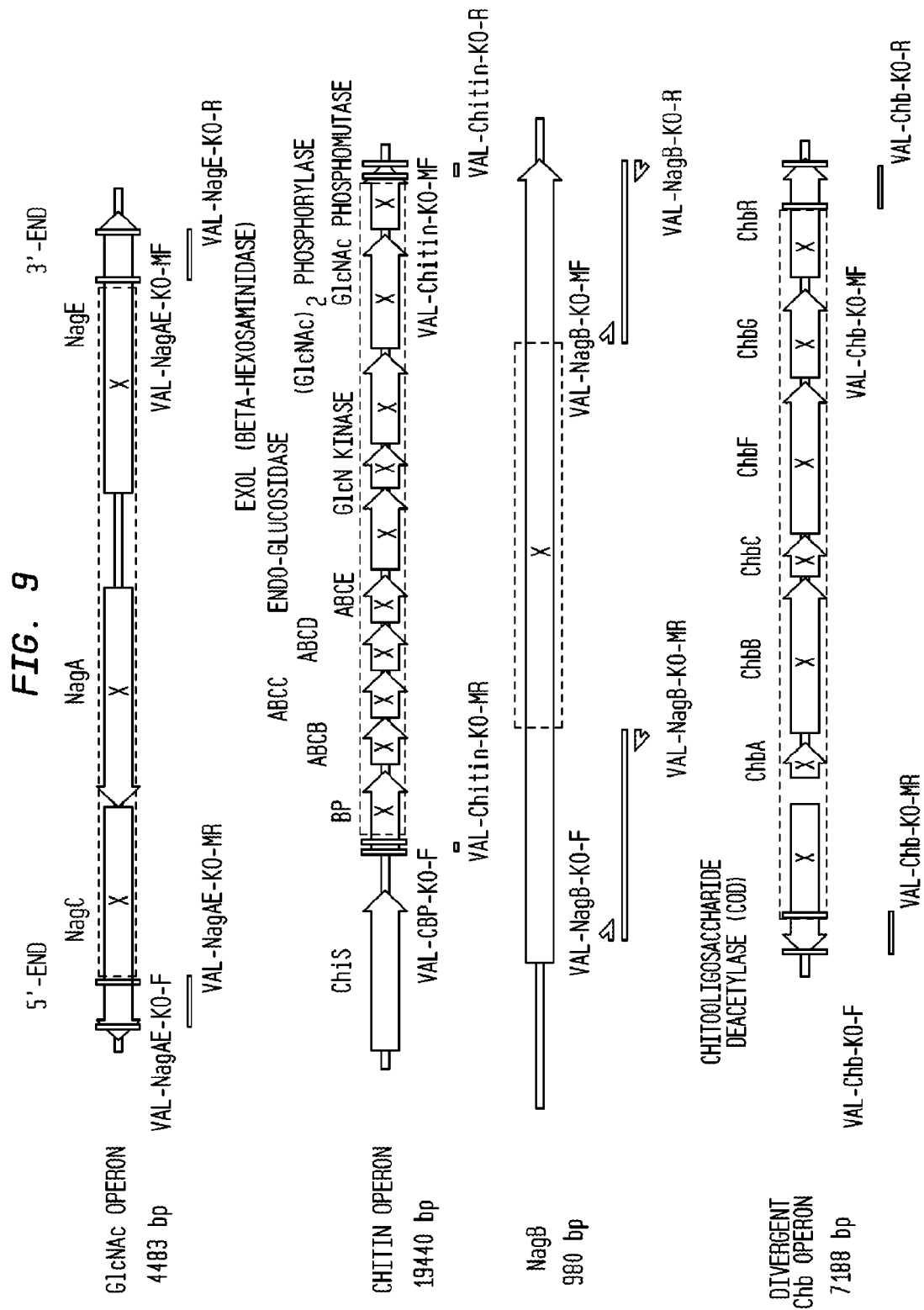

FIG. 9 shows the gene knockout strategy outlined in FIG. 8 in more detail. Note that the chitin catabolic operon is deleted, including BP, the first gene in the operon, but ChiS is not deleted, and is therefore always ON. The Figure schematically illustrates the genes in 3 operons: GlcNAc, chitin, and Chb (acronym for chitobiose ((GlcN)$_2$)). The genes in these operons express proteins involved in the transport and degradation of GlcNAc, and the disaccharides (GlcNAc)$_2$ and (GlcN)$_2$. The two disaccharide transporters were deleted to avoid loss of (GlcNAc)$_2$. (X=knockout)

Figure 10:
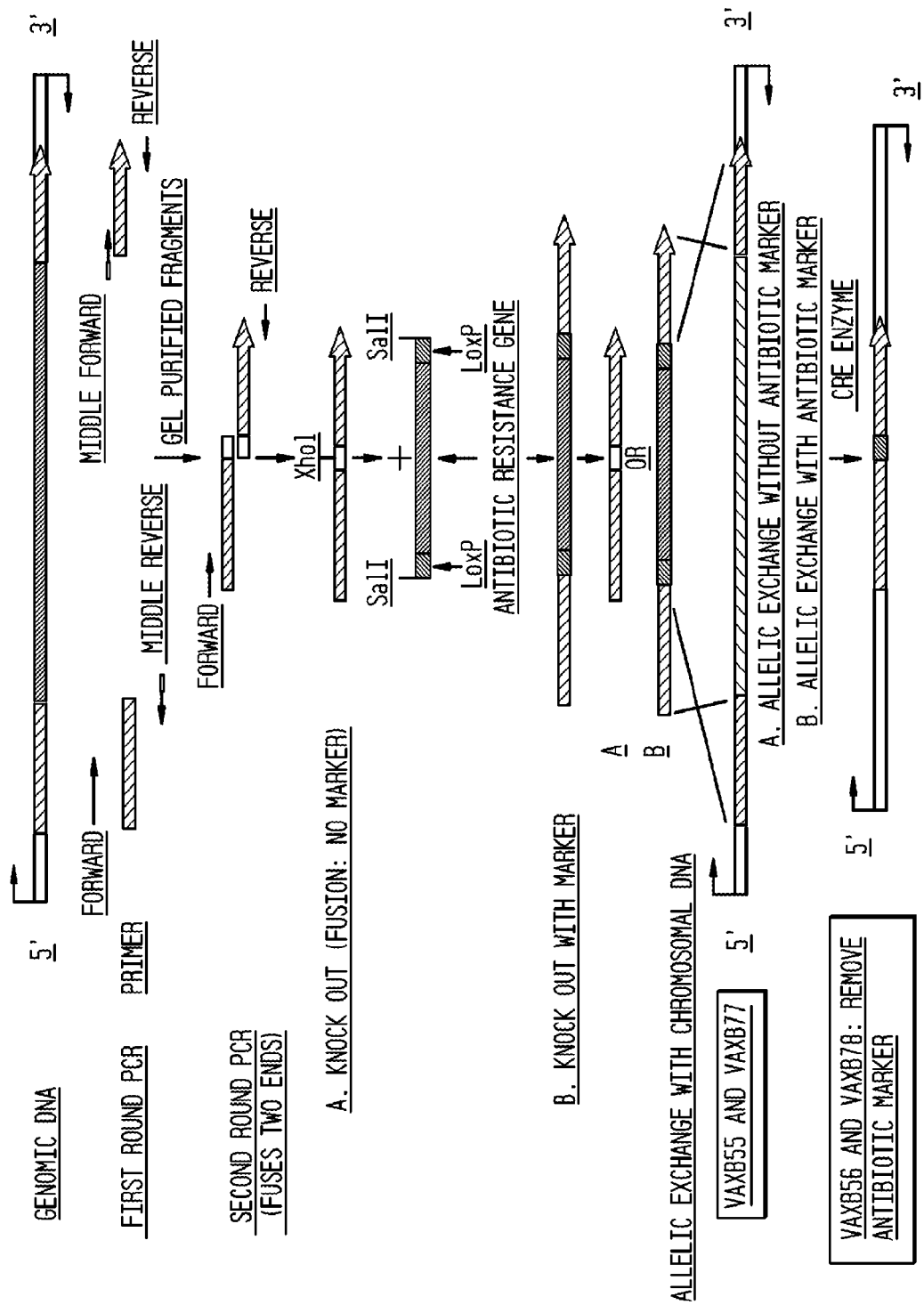

FIG. 10 shows the general experimental approach taken to complete the knockout strategy described in FIG. 9 in more detail.

Figure 11:
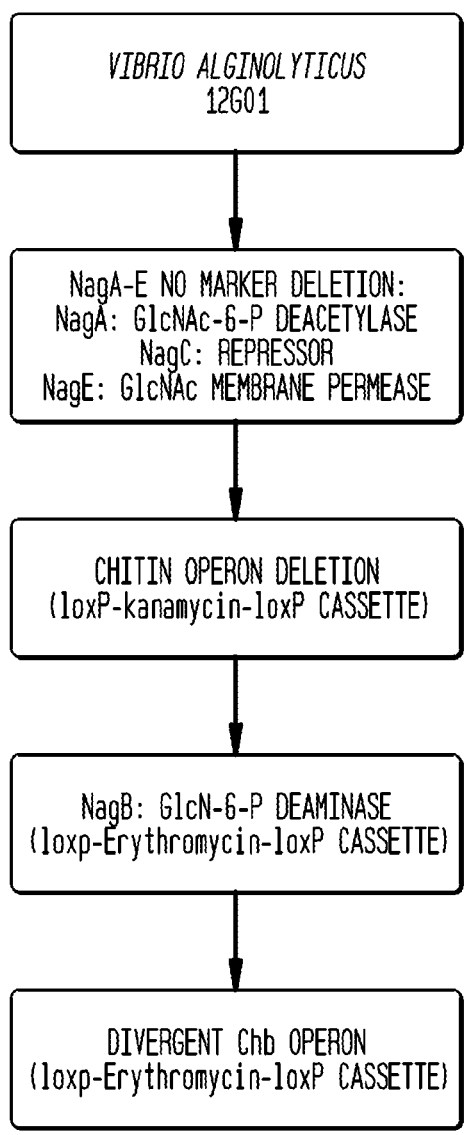

FIG. 11 is a summary of the knockout for *Vibrio alginolyticus* 12G01.

Figure 12:
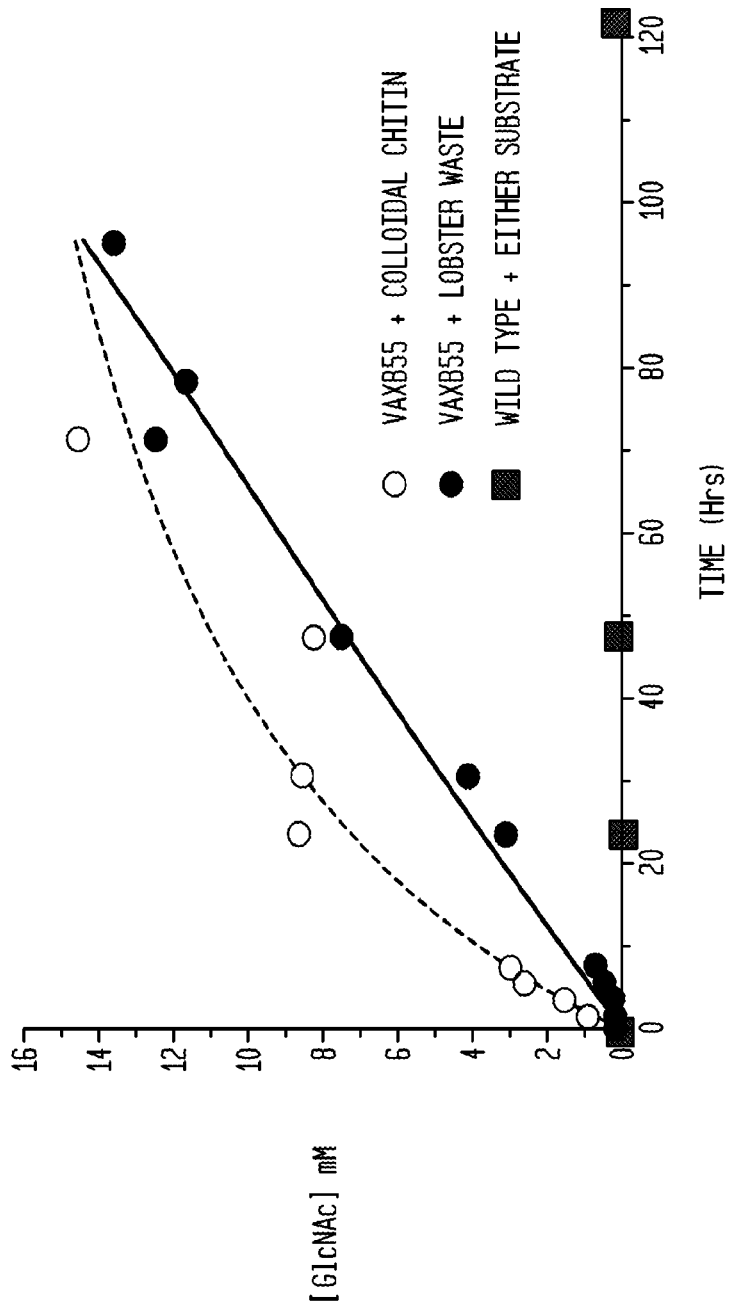

FIG. 12 shows GlcNAc production from wild type *V. alginolyticus* and the mutant strain (VAXB55) incubated with colloidal chitin or lobster waste. Over a period of days virtually no GlcNAc was observed with wild type cells because they consumed it as rapidly as it was formed. On the other hand, the mutant produced GlcNAc from both substrates. These results were obtained in flask cultures.

Figure 13:
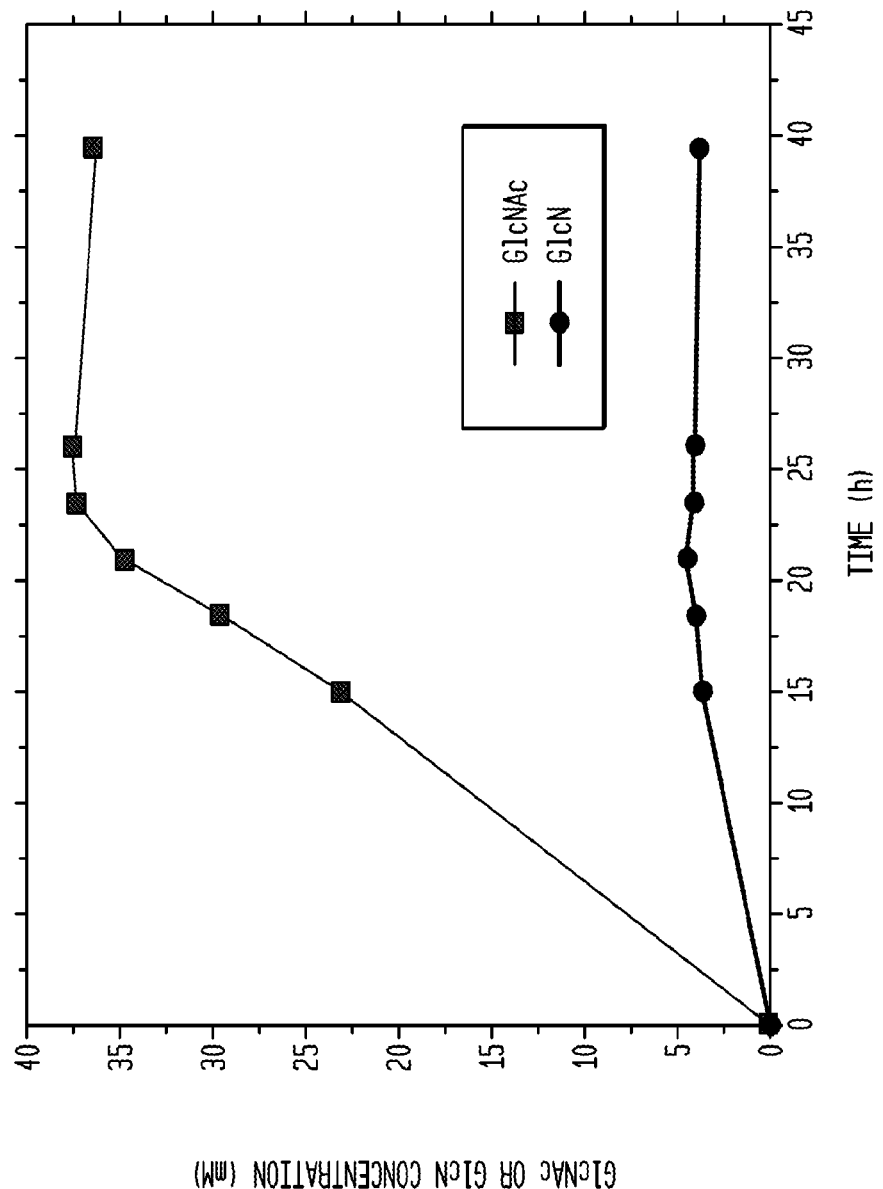

FIG. 13 shows the yields of both GlcNAc and GlcN from lobster waste. The yield of GlcNAc was about 93%. A small amount of GlcN was also obtained. With VAXB77, the GlcN yield was about 10% of the GlcNAc yield.

Figure 14:
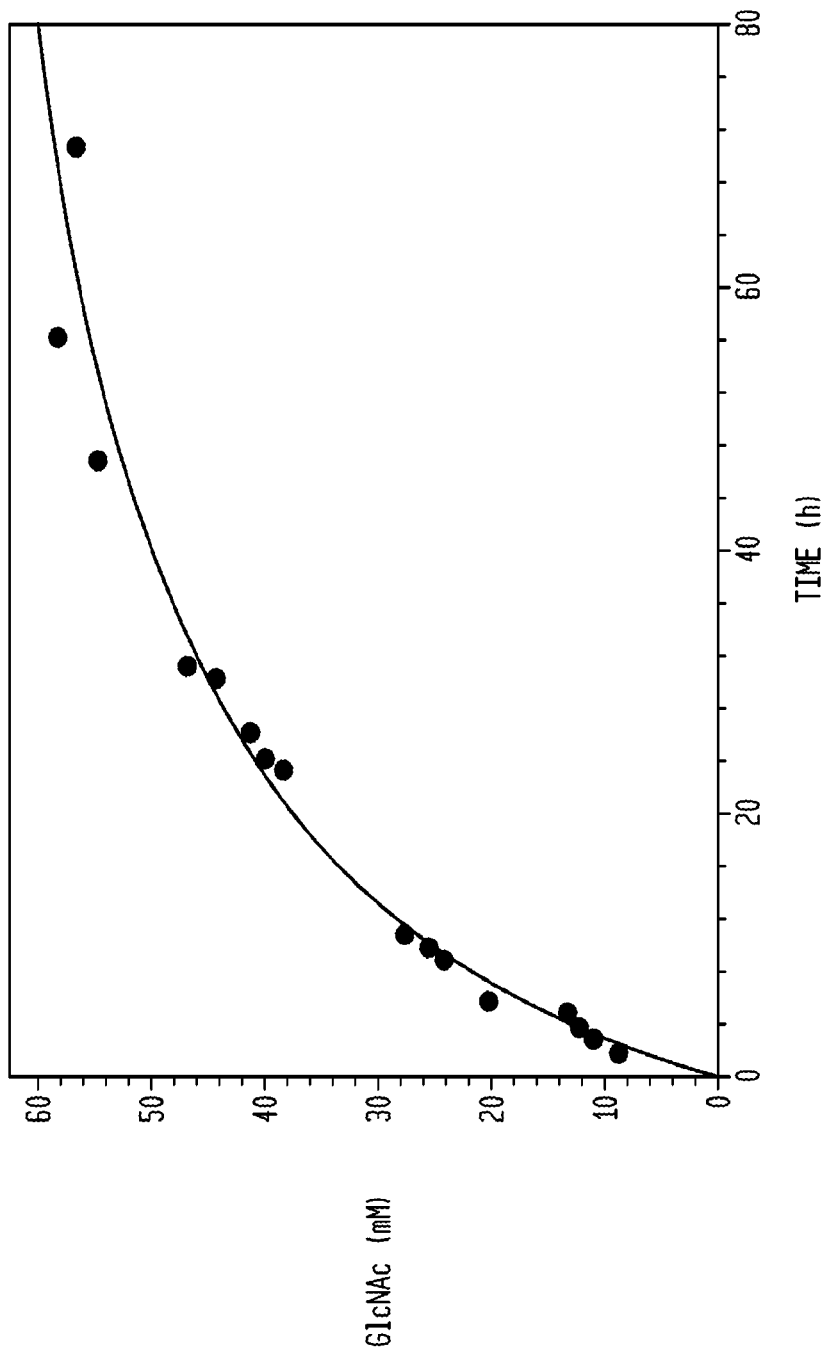

FIG. 14 shows the results of fermentation of shrimp shell waste by the mutant VAXB77 in jar type fermentors. The actual yield of GlcNAc was consistent with the theoretical value. The GlcN yield was 5-6% compared to the GlcNAc.

Figure 15:
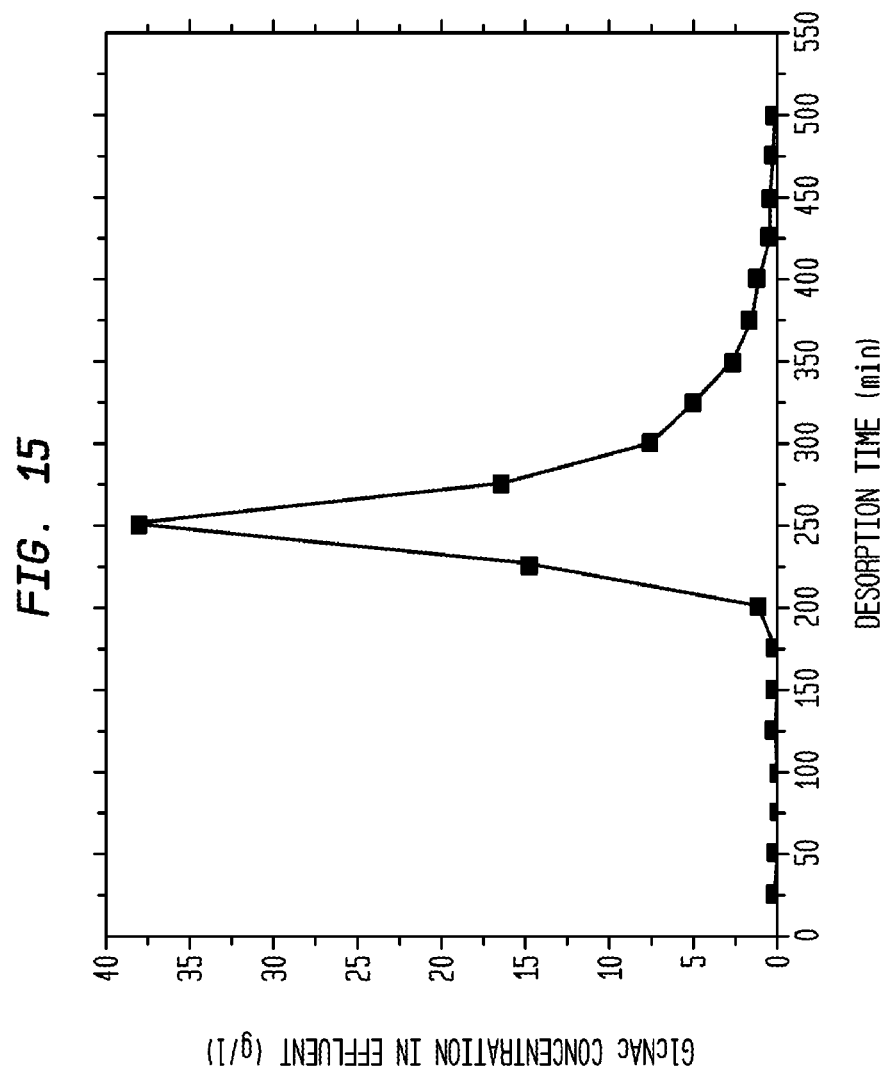

FIG. 15 shows the product of desorption of the GlcNAc fermentation product from a charcoal column; 200 g of activated charcoal was used. All GlcNAc was adsorbed by the charcoal. One liter of 50% ethanol was used for desorption at a flow rate of 2 ml/min. The y axis is GlcNAc concentration in effluent (g/l) and the X axis is the desorption time (minutes).

Figure 16A:
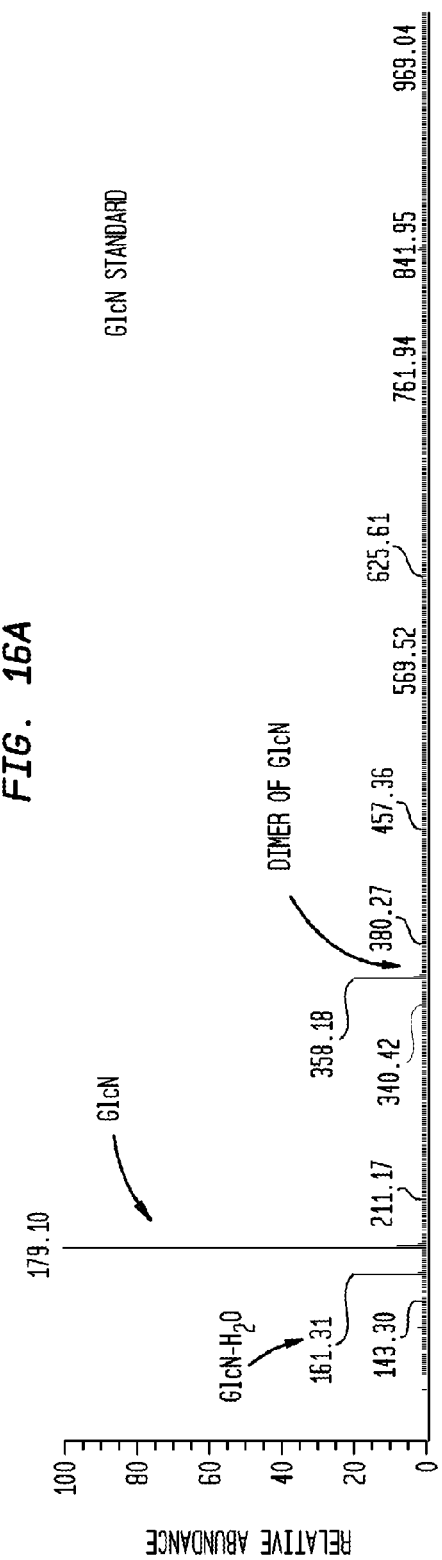
Figure 16B:
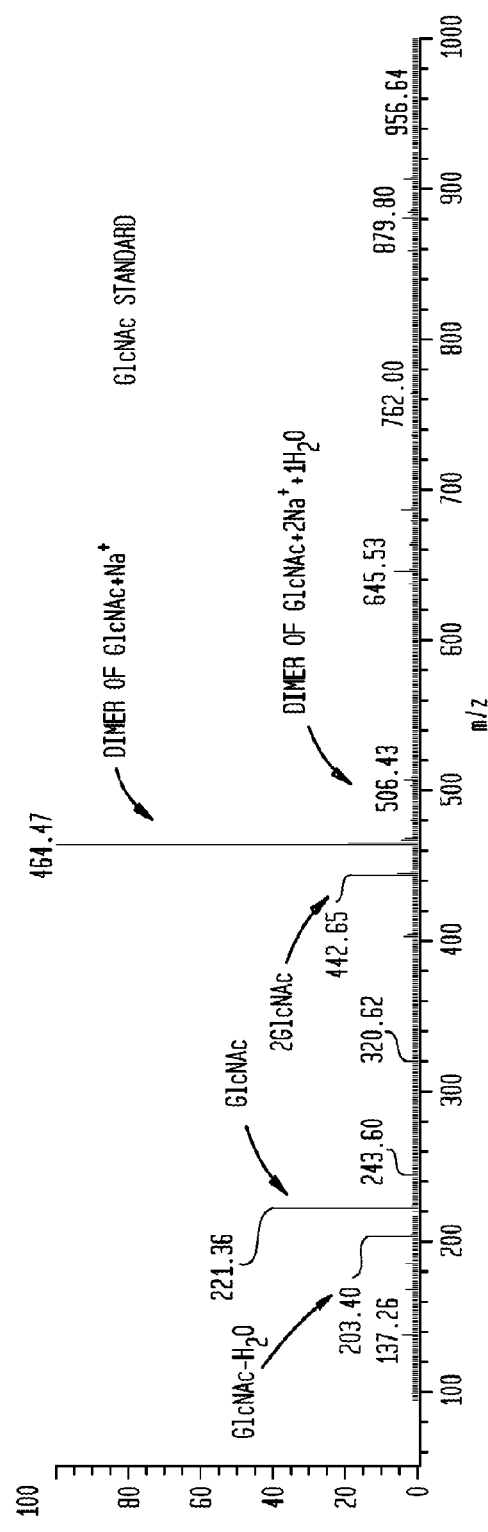

FIGS. 16A and B show how purity of GlcNAc was assessed by electrospray-mass spectroscopy (ESI-MS). FIG. 16A shows the results for GlcN. FIG. 16B shows the results for GlcNAc.

Figure 17A:
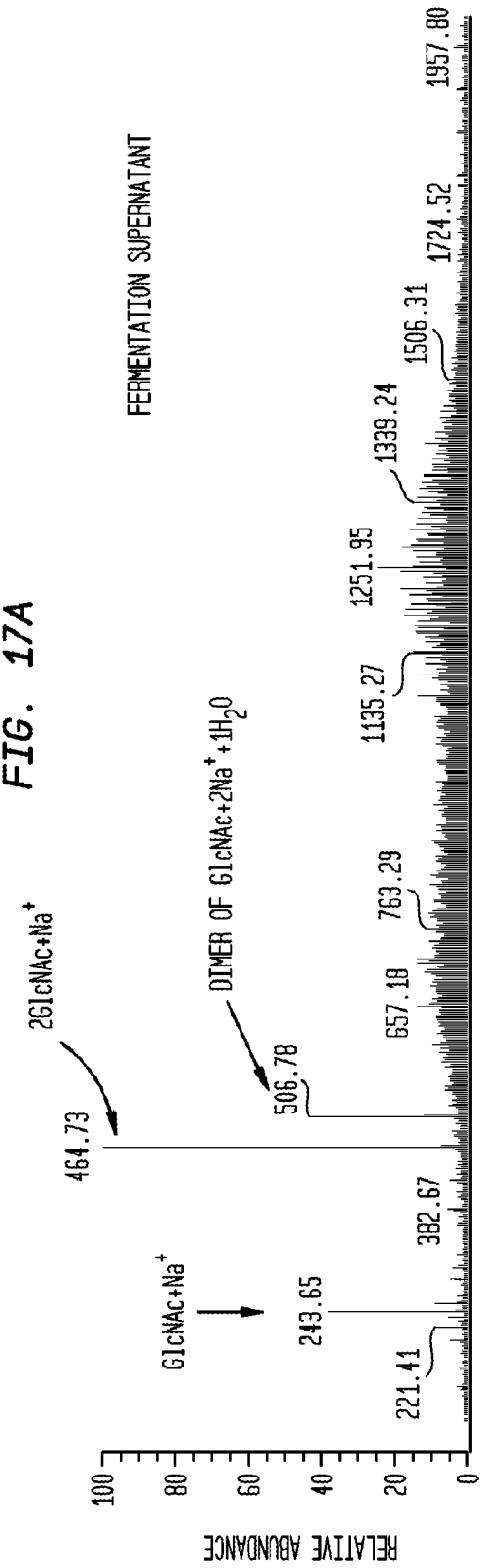
Figure 17B:
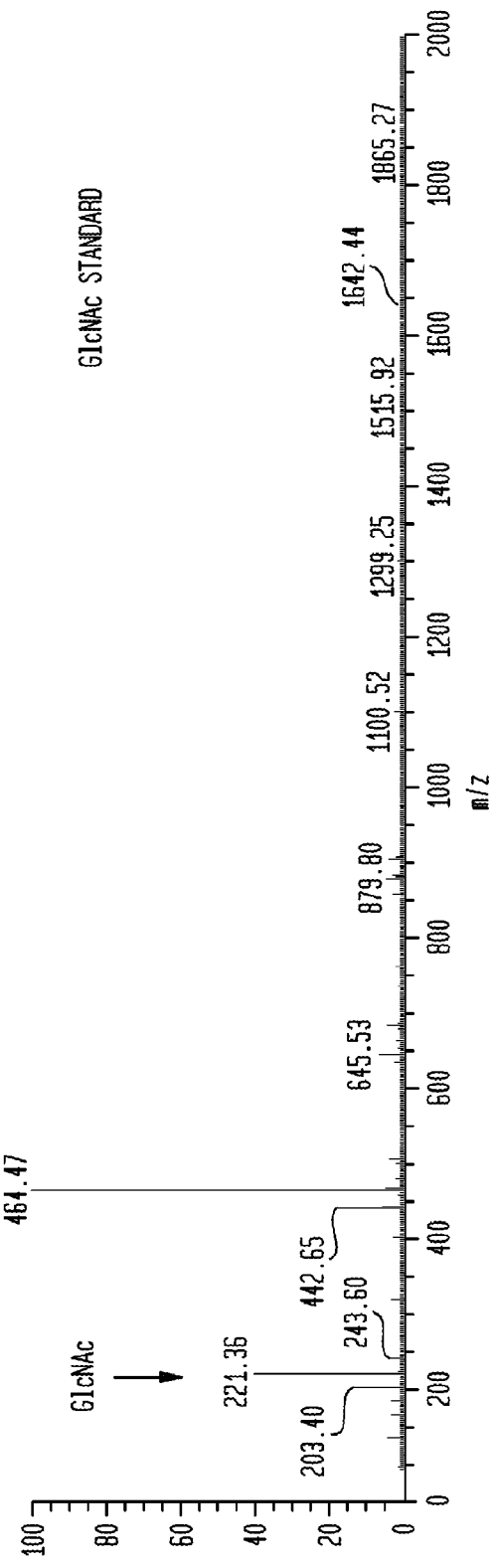

FIGS. 17A and B show that the major component of the fermentation of the shrimp waste is GlcNAc. The concentration of GlcN, if present, was too low to be detected. FIG. 17A shows that the components of the fermentation supernatant are closely similar to that of the GlcNAc standard (FIG. 17B).

FIGS. 18A and B show the amount of GlcNAc isolated from fermentation supernatant and purified on a charcoal column.

FIG. 18A shows ESI-MS of the fermentation broth supernatant fluid placed on the column, and FIG. 18B shows the 50% alcohol eluate of the column. A single step is sufficient to give a high yield of nearly pure GlcNAc.

Figure 19:
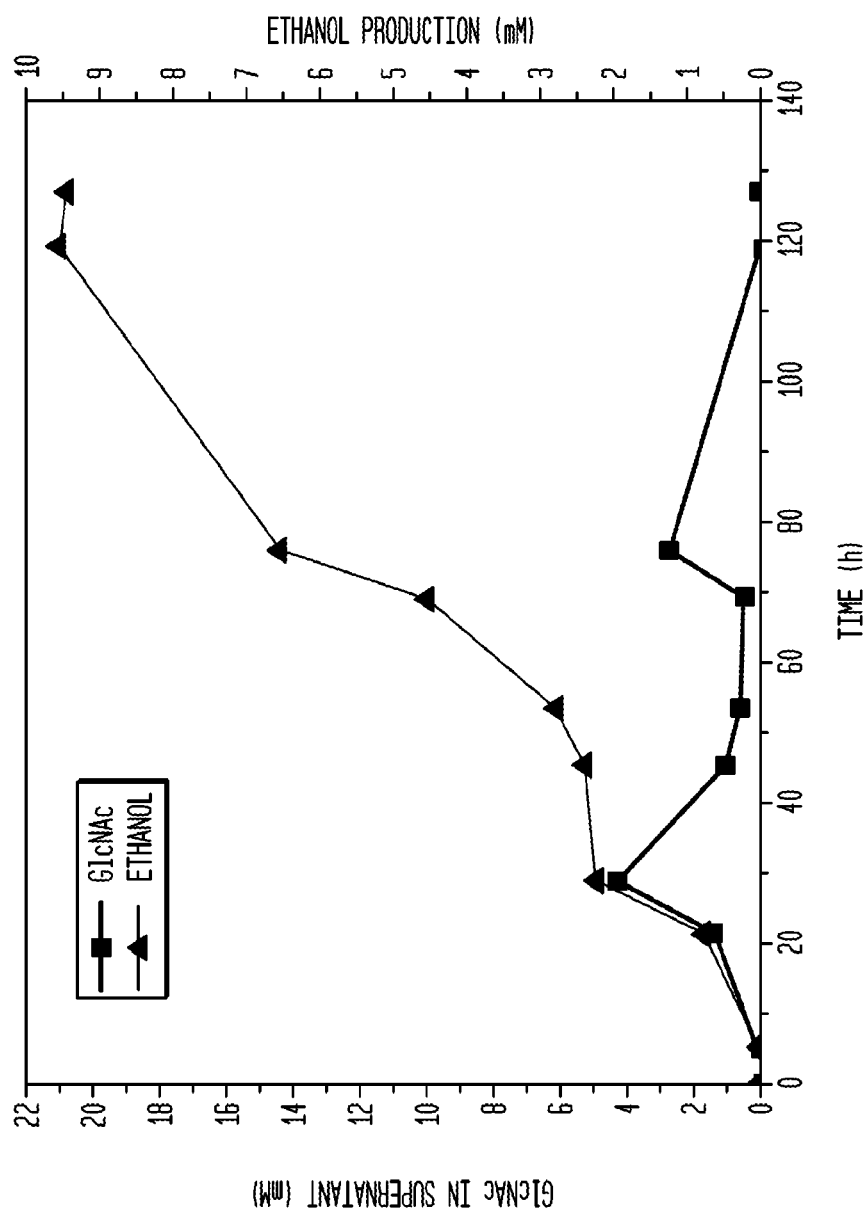

FIG. 19 shows that the results of co-fermentation of *V. alginolyticus* mutant (VAXB77) and *S. cerevisiae* (mutant S9) in a fermentor where the initial GlcNAc concentration as chitin was about 22 mM. After 5 days of co-fermentation, the final ethanol concentration was about 9.6 mM.

DETAILED DESCRIPTION OF THE EMBODIMENTS

Embodiments of the invention include methods for (a) metabolizing environmental chitin into GlcNAc; (b) converting N-acetylglucosamine to glucosamine; and (c) converting GlcNAc to ethanol.

(a) Conversion of Chitin in Chitin-Containing Waste Products into N-Acetylglucosamine Chitin in chitin-containing waste products, which include fungi and invertebrate exoskeletons, for example seafood waste, such as crab, lobster, or shrimp, can be converted to GlcNAc by engineering the appropriate genes in bacteria (such as Vibrionaceae) that actively consume chitin. Large amounts of chitin waste are also generated from fungal cell walls. For example, waste fungi from fermentation of *Aspergillus* strains which have a large amount of chitin in their cell walls and are used for industrial processes is a chitin source for generating GlcNAc and GlcN. Algae are also a rich source of chitin.

Bacteria capable of converting chitin to GlcNAc includes gram negative bacteria such as Vibrionaceae for example *V. furnissii*, *V. cholera* and *V. alginolyticus* (Yu and Roseman, "Bacterial adhesion to immobilized carbohydrates", *In Lectins and Glycobiology*, Gabius, ed. Springer-Verlag) (1993)).

Knockouts of selected genes in bacteria yielded mutants that converted chitin-containing waste products to GlcNAc and small amounts of GlcN. Vibrionaceae mutants were created in which the catabolic pathway in the cytoplasm for converting GlcNAc to fructose-6-P was disrupted by knocking out specific genes resulting in accumulation of GlcNAc in the extracellular fluid (see FIGS. 8-10).

Gram negative bacterial cells which include Vibrionaceae have 3 compartments: the extracellular compartment, the periplasmic space, and the cytoplasm. The extracellular and periplasmic compartments are separated by the cell wall/outer membrane complex. This complex contains pores which permit low molecular weight solutes to penetrate into the periplasm. The periplasm (from 20-30% of the cell volume) and cytoplasm are separated by the cytoplasmic membrane, which contains the various transporters or permeases and many other proteins.

Figure 1:
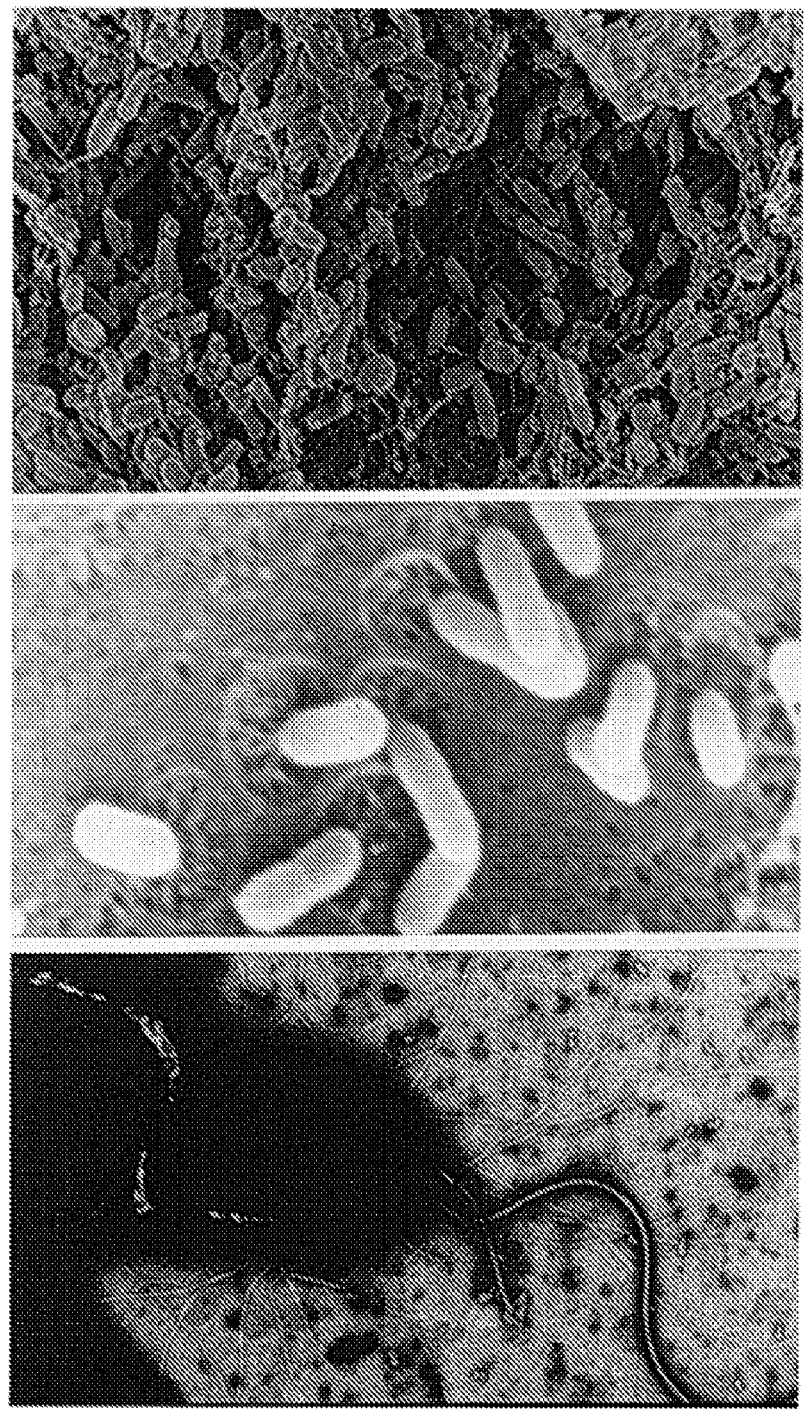
FIG. 1 shows three electron micrographs (a) a section of a single *Vibrio* cell, (b) *Vibrios* digesting a crab shell, and (c) marine snow, which resembles a huge bacterial colony as the bacteria grow on the agglutinated copepod skeletons.
Figure 2:
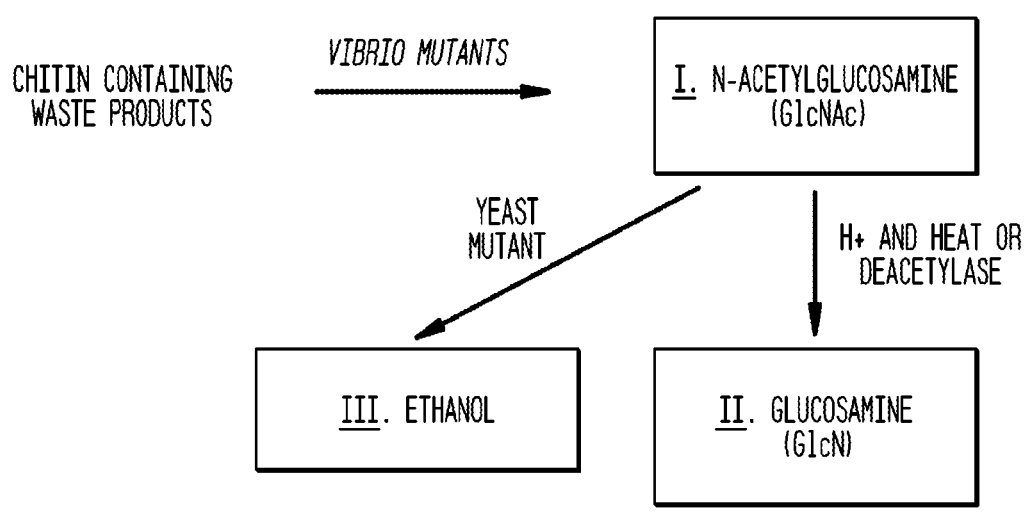
FIG. 2 provides an overview of the conversion of chitin containing waste products into GlcNAc, GlcN or a biofuel. Vibrionaceae mutants break down the chitin to predominantly GlcNAc. The GlcNAc may then be treated by a deacetylase to produce GlcN (Roseman, J. Biol. Chem. 226: 115-124 (1957) or by acid or heat. Alternatively, the GlcNAc may be further metabolized to ethanol preferably using an engineered yeast.

Wild type Vibrionaceae produce proteases for digesting insoluble proteins that enmesh chitin thereby releasing chitin substrate. The cells secrete extracellular chitinases and proteases (see FIGS. 1 and 5) which attack the cuticle and hydrolyze the chitin to chitin oligosaccharides, (GlcNAc)$_n$. Expression of the extracellular enzymes is under stringent cellular control. The examples provided herein describe the use of several different Vibrionaceae. In one embodiment, *V. alginolyticus* is described and is convenient for use in generating GlcNAc as it is non-pathogenic. It is obtained from a marine environment. Its genome sequence is described in Genebank (accession number AAPS00000000, see below).

Extracellular chitin is digested by chitinases to soluble oligosaccharides. These are taken up by the wild type bacteria through pores in the membranes identified as porins (Keyhani *J. Biol. Chem.* 275: 33068-33076 (2000)) and some of them are hydrolyzed to GlcNAc by an outer membrane bound β-N-acetylglucosaminidase (EC 3.2.1.52). Once in the periplasmic space, the oligosaccharides are hydrolytically cleaved by two enzymes, a chitodextrinase (D in Figure) and a specific β-N-acetylglucosaminidase (E in FIG. 4) (Keyhani and Roseman *J. Biol. Chem.* 271, 33414-33424 (1996); Keyhani and Roseman *J. Biol. Chem.* 271: 33425-33432 (1996)). The combined action of the two enzymes yield as final products, the monosaccharide, GlcNAc, and the disaccharide, (GlcNAc)$_2$. The periplasmic β-N-acetylglucosaminidase (E) is an exoenzyme that has significantly greater activity with the chitooligosaccharides (GlcNAc)$_n$, where n≥3 at the pH of sea water. But, (GlcNAc)$_2$ is not significantly hydrolyzed by this enzyme and can thus serve as the signal for the sensor. GlcNAc uptake and catabolism in *Vibrio* is essentially the same as in *E. coli* (FIG. 3).

Figure 3:
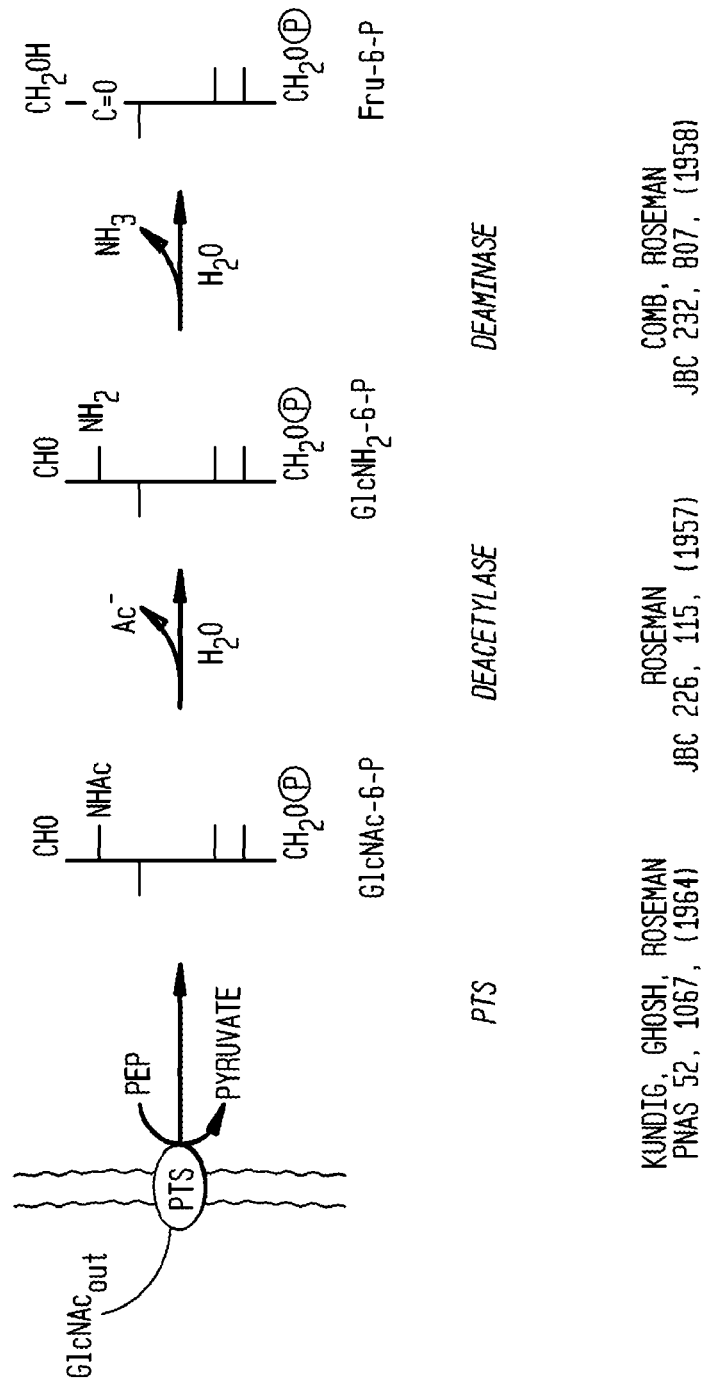
FIG. 3 provides the catabolic pathway in *Escherichia coli* (*E. coli*) for the conversion of GlcNAc and GlcN to fructose-6-phosphate in the cytoplasm. In *E. coli*, GlcNAc traverses the periplasmic space, and is taken up by the phosphoenolpyruvate: glycose phosphotransferase system (PEP) (Kundig et al. *Proc. Natl. Acad. Sci., U.S.A.* 52: 1067-1074 (1964)) at the cytoplasmic membrane. The transport product in the cytoplasm is GlcNAc-6-P. The acetyl group is then removed, giving GlcN-6-P (Distler et al. *J. Biol. Chem.* 230: 497-509 (1958); Roseman *J. Biol. Chem.* 226: 115-124 (1957)). This is further converted to fructose-6-P and $NH_4^+$ (Comb and Roseman *Biochim. et Biophys. Acta* 21: 193-194 (1956); Comb and Roseman *J. Biol. Chem.* 232: 807-827 (1958)).
Figure 4:
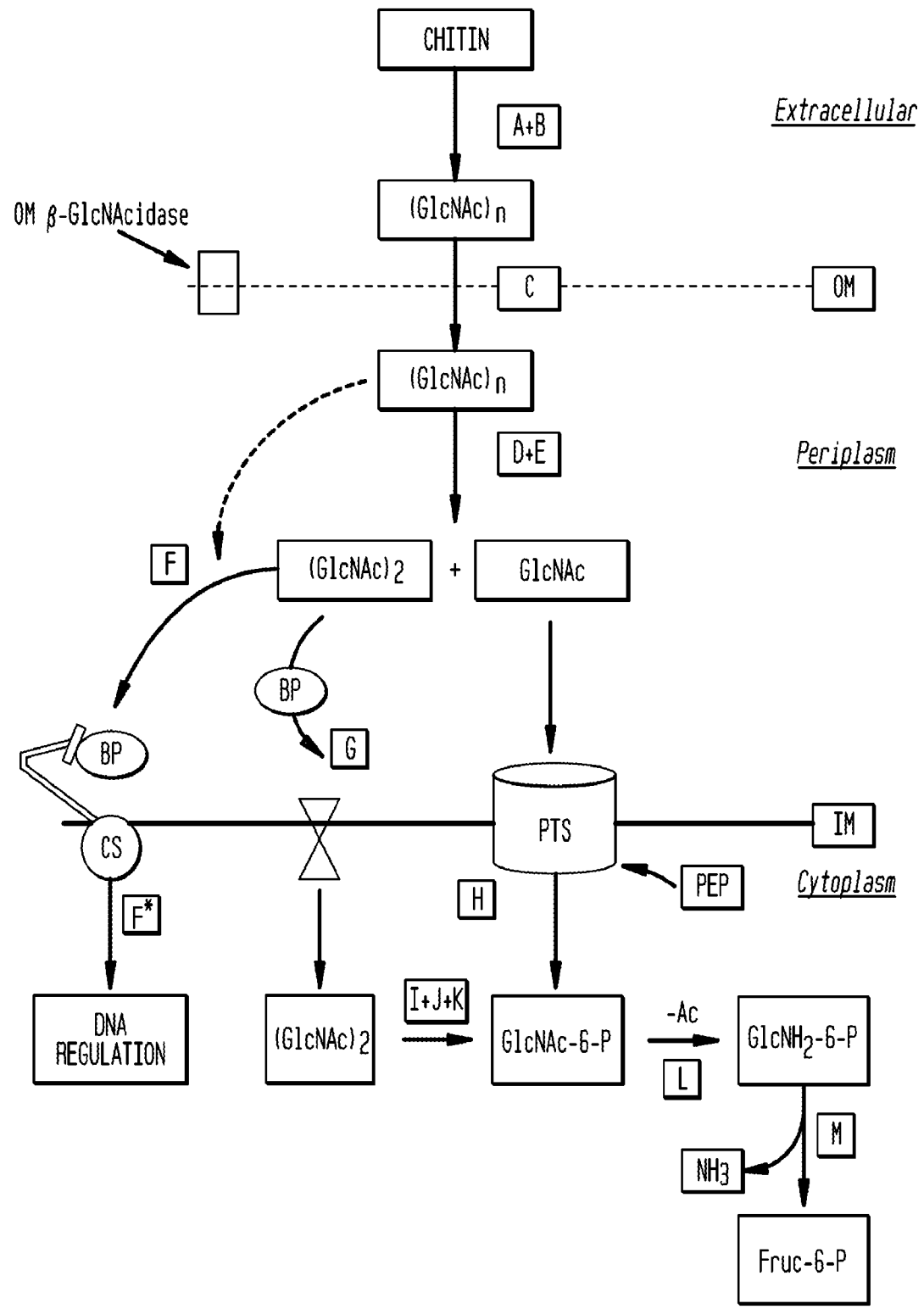
FIG. 4 shows the cascade of reactions that converts chitin to fructose-6-P in Vibrionaceae as the pathway extends from the extracellular space, through the periplasm and into the cytoplasm.

In wild type organisms, GlcNAc monosaccharides may be translocated from the periplasmic space into the cytoplasm by means of the phosphoenolpyruvate: glycose phosphotransferase system (PTS in FIG. 3). This system, (H in FIG. 4), catalyzes the vectorial transport of sugars such as GlcNAc across the membrane, with the energy supplied by phosphoenolpyruvate (PEP) (Bouma and Roseman *J. Biol. Chem.* 271: 33457-33467 (1996); (Bouma and Roseman, 1996a; Heidelberg et al. *Nature* 406(6795): 477-483 (2000)).

GlcNAc disaccharides may be translocated from the periplasmic space into the cytoplasm by an ABC transporter (FIGS. 4 and 6), driven by ATP hydrolysis (Keyhani et al. *J. Biol. Chem.* 271: 33409-33413 (1996)). The first step takes place in the periplasm, where the disaccharide binds to a BP. BP binds to the disaccharide and delivers it to the ABC transporter (G in FIG. 4). The disaccharide can then be translocated into the cytoplasm without modification. The sum of the next 3 steps, I+J+K, is to convert (GlcNAc)$_2$ to GlcNAc-6-P. Briefly: I is a phosphorylase that converts (GlcNAc)$_2$ to GlcNAc-1-P+GlcNAc (Park et al. *J. Biol. Chem.* 275: 33077-33083 (2000); Enzyme 3 is an ATP kinase specific for GlcNAc. The GlcNAc-1-P is converted to GlcNAc-6-P by Enzyme K, an N-acetylglucosamine-phosphate mutase (EC: 5.4.2.3) specific for interconverting GlcNAc-6-P and GlcNAc-1-P.

Figure 5:
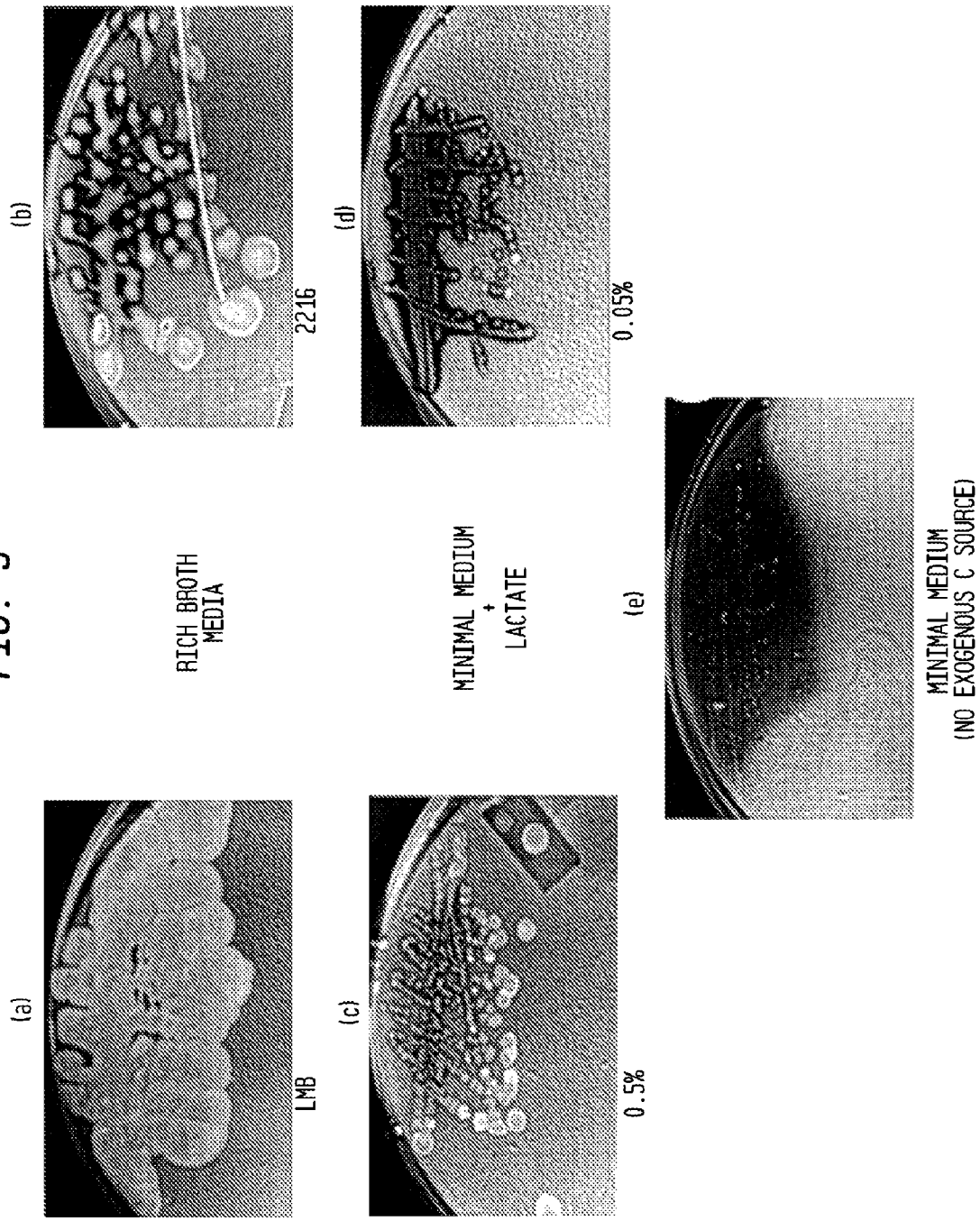

The expression of the chitin metabolism genes briefly outlined above is stringently regulated in Vibrionaceae. For example, FIG. 5 shows wild type cells growing on the surface of Petri dishes. In this experiment, the cells were streaked on agar plates containing the indicated carbon sources. The agar was overlaid with colloidal chitin, which appeared white in FIG. 5A-5E. Expression of extracellular chitinases by the colonies was evident as clear zones around the colonies. When the medium in the agar was a rich broth, there was heavy growth of the *Vibrio* species, but no clear zones. A somewhat less rich carbon source, again gave good growth, with little evidence of chitinases. On a synthetic medium containing 0.5% lactate as a carbon source, there was again good growth with little chitinase production. When the carbon source was dropped to 0.1% lactate, growth was reduced, and clear zones were now evident indicating expression of chitinases. Finally, when is the cells were exposed only to the chitin (no other carbon source), there were large clear zones, and it was in fact, difficult to see the tiny colonies. In other words, a combination of starvation and exposure to chitin lead to high expression of the chitinases.

This regulation is largely controlled by a two-component His kinase system. In fact, according to results obtained by DNA microarray analysis (Meibom et al. *Proc. Natl. Acad. Sci. U.S.A* 101: 2524-2529 (2004)), the expression of about 200 genes is controlled by this sensor when the cells grow on chitin. FIG. 6 illustrates the structural units in ChiS, and how ChiS functions. An important component of the signal transmission is BP specific for chitooligosaccharides, but not GlcNAc. BP binds to the periplasmic loop of ChiS, and under these circumstances, ChiS is in the negative mode, i.e., no signaling (FIG. 6). However, when extracellular chitinases hydrolyze chitin in the environment, the major product (GlcNAc)$_2$ enters the periplasmic space, and competes with ChiS for BP. When BP is released from ChiS, the latter is turned "ON" (FIG. 7), which means that ChiS signals the 200 or so genes to be expressed or repressed including the chitinases and N-acetylglucosaminidases. Thus, it is the environmental signal, (GlcNAc)$_2$, that gives this dramatic response.

The mutant Vibrionaceae described herein have been engineered to produce chitinases continuously under substantially all growth conditions. Transport systems for GlcNAc and chitooligosaccharide have been knocked out without preventing the mutant Vibrionaceae from metabolizing an alternative food source or interfering with other machinery in the cell. These cells are expected to grow well on waste products since these products contain protein, etc., similar to the broth medium, which supports rapid growth of the cells. In embodiments of the invention, chitinase production and secretion is preferably turned on all the time, independent of the other substances in the medium. This has been accomplished by knocking out BP, which means that ChiS is permanently turned ON as in FIG. 7. The conversion of chitin to GlcNAc by these knockout mutants is shown in FIGS. 12-15, 16A-B, 17A-B, 18A-B and 19.

(b) Conversion of N-Acetylglucosamine into Glucosamine, HCl

GlcNAc can be converted to GlcN by a deacetylase (Roseman *J. Biol. Chem.* 226: 115-124 (1957)). Provided here is an alternative procedure that utilizes mild acid hydrolysis (see Example 3). It is also contemplated that conversion of GlcNAc to GlcN may be achieved during microbial fermentation.

(c) Conversion of N-Acetylglucosamine into Ethanol

An important use of chitin is its conversion to ethanol via GlcNAc. While common yeasts, such as *Saccharomyces cerevisiae* (*S. cerevisiae*) cannot utilize GlcNAc (or GlcN), an engineered *S. cerevisiae* is used here that metabolizes GlcNAc to produce ethanol (see, for example PCT/US09/064,511). We have shown that this engineered *S. cerevisiae* produced ethanol from GlcNAc almost as rapidly as from glucose (see Table 4 and FIG. 19). Ethanol production proceeded both aerobically and under O$_2$ limiting conditions and similar yields of ethanol were obtained with GlcNAc and with Glc. This can be achieved in either a separate or a combined fermentation by: (a) Isolating the GlcNAc and adding it to yeast growth medium as in Table 4; (b) Following the first fermentation with the *V. alginolyticus* mutant and then adjusting the supernatant with yeast growth medium as in Table 3; or (c) Co-culturing the yeast and *Vibrio* mutants with chitin as in FIG. 19.

We found that: (a) *V. alginolyticus* mutants utilize metabolites of *S. cerevisiae* including acetate, a byproduct of the alcoholic fermentation; (b) *V. alginolyticus* mutants can survive in ethanol medium generated by the yeast; and (c) growth and fermentations for both *Vibrio* and yeast can occur at a common temperature and pH.

It was demonstrated here that a charcoal column is very effective in providing an efficient simple and effective purification of GlcNAc from fermentation media. This does not preclude however, the use of other methods of purification not described here but known in the art.

Uses of GlcNAc include its conversion into ethanol for use as a biofuel, its conversion into GlcN for use as a nutraceutical, or as a cosmetic. For example, cosmetics may include skin whitening and anti-wrinkle GlcN formulations where the formulations may be topical creams or ingestible products.

All references cited herein, including U.S. Provisional Application No. 61/172,251 filed Apr. 24, 2009, are incorporated by reference.

EXAMPLES

Example 1

Production of Extracellular GlcNAc

Mutants from *V. alginolyticus* were constructed that catabolized waste products, and hydrolyzed the chitin to produce GlcNAc. These mutants could not utilize GlcNAc as a nutrient. *V. alginolyticus* 12G01 wild type strain was isolated from the surface water at Plum Island Ecosystem-LTER, USA, by Dr. Martin Polz (Stocker et al. *Proc. Natl. Acad. Sci. U.S.A* 105: 4209-4214 (2008); Hunt et al. *Appl. Environ. Microbiol.* 74: 44-51 (2008)). This strain is naturally resistant to 100 µg/ml ampicillin, but sensitive to other antibiotics. This organism consumes chitin from waste products. The genome sequence is provided in the Gordon and Betty Moore Foundation Marine Microbial Genome Sequencing Project and deposited under Accession No. AAPS00000000. No genome annotation was provided in the public database or published papers.

Genetic Manipulation

Standard molecular biological methods and techniques were used unless otherwise indicated. The acronym VAL is used to indicate *V. alginolyticus* in the Table and Figures.

*V. alginolyticus* 12G01 was transformed by transconjugation. The target genes are listed in FIGS. 8 and 9, and the general procedures for deleting a target gene are outlined in FIG. 10. The primers used are listed in Table 1.

TABLE I

| VAL-NagAE-KO-F | GCAGATCTCGTTGGCTGCTTATCA (SEQ ID NO: 1) |
|---|---|
| VAL-NagAE-KO-MR | AGTAGCTCGAGATGTCAGCACGCAATGA (SEQ ID NO: 2) |
| VAL-NagAE-KO-MF | GACATCTCGAGCTACTTCGTGTTCCGTA (SEQ ID NO: 3) |
| VAL-NagE-KO-R | CTAGCTTCACAACTCCCATAG (SEQ ID NO: 4) |
| VAL-NagB-KO-F | GCGAGATCTAGCAGCACAAGTAGGTA (SEQ ID NO: 5) |
| VAL-NagB-KO-MR | ATGGCTCGAGGATGCCAATGTACTCA (SEQ ID NO: 6) |
| VAL-NagB-KO-MF | GCATCCTCGAGCCATAACAAAGCTCAG (SEQ ID NO: 7) |
| VAL-NagB-KO-R | GCGGAGATCTGCCTTTGATGTTTCTGC (SEQ ID NO: 8) |
| VAL-BP-KO-F | GGAGATCTACAGCACTAGCAACAGCA (SEQ ID NO: 9) |
| VAL-Chitin-KO-MR | CAGACCTCGAGCGAAATACAGGCGTGT (SEQ ID NO: 10) |
| VAL-Chitin-KO-MF | ATTTCGCTCGAGGTCTGAGTTGCTGGAT (SEQ ID NO: 11) |
| VAL-Chitin-KO-R | AGATCTGAAGAACACGTTCCGCAG (SEQ ID NO: 12) |

TABLE I-continued

| VAL-Chb-KO-F | AAGATCTGAGTGTTCGGAGTCCAG (SEQ ID NO: 13) |
|---|---|
| VAL-Chb-KO-MR | CATCCTCTCGAGTACCTAAGCTCGCTAA (SEQ ID NO: 14) |
| VAL-Chb-KO-MF | AGGTACTCGAGAGGATGCTGGTATAGA (SEQ ID NO: 15) |
| VAL-Chb-KO-R | GGAGATCTAAGGAGCGATCTGCTTTG (SEQ ID NO: 16) |

Construction of Knockout Vectors

The suicide vector and transconjugation methods were used to construct the required deletions and knockout mutants. In this procedure, a deletion construct, with or without an antibiotic marker, was prepared as outlined in FIGS. 8-11. The desired DNA fragment was then transferred to a general suicide vector pRE113 (Edwards, et al. *Gene* 207: 149-157 (1998)). pRE113 was developed from plasmid pRE112 (ATCC 87692). pRE113 is a plasmid with a BglII restriction site inserted into the SmaI site of pRE112. These vectors contained a conditional origin of replication, R6K. For the vectors to be replicated, a host cell, such as *E. coli* S17-1, was used which expressed the pi protein in trans.

When *E. coli* S17-1 containing the desired vector was mixed with virtually any Gram negative cell such as a Vibrionaceae, the cells mated and the vector was transferred to the recipient Vibrionaceae cell. In the Vibrionacea cells used here, no pi protein was generated, and the vector DNA could not replicate (therefore called a suicide vector), unless it was integrated into the chromosome by allelic exchange of the homologous DNA.

In the final selection, only the Vibrionacea cells with the desired deletions in the chromosome survived.

A two-step selection method was also used. In the first step, using the antibiotic markers, only the Vibrionacea cells were selected that contained the entire plasmid integrated into the chromosome. In the second step, the sacB1 gene, which was carried by the suicide plasmid, was used. This gene expressed a periplasmic sucrase that was lethal to the cell in the presence of sucrose (Blomfield et al. *Mol. Microbiol.* 5: 1447-1457 (1991)) and was used as a positive selection marker.

The general strategy for making the constructs is outlined in FIG. 10. It included a two-step PCR to get the knockout construct with wild type genomic DNA as the template. Then the construct was subcloned into pGEM-T vector (Promega, Madison Wis.). Depending on the construct, an antibiotic cartridge ending with the SalI site was inserted into the XhoI site. The BglII fragments from the above constructs were inserted into the BglII site in pRE113 giving the final suicide knocking out constructs.

1. pRE113-VAL-Nag OperonΔ:

First round PCR was with primer pairs VAL-NagAE-KO-F/VAL-NagAE-KO-MR and VAL-NagAE-KO-MF/VAL-NagE-KO-R. The second round bridge PCR was with primers VAL-NagAE-KO-F/VAL-NagE-KO-R. The resulting construct had a 6 bp XhoI insertion at the middle: 910 bp out of 1212 bp had been removed from the nagC (Repressor), the complete nagA (GlcNAc-6-P deacetylase) and 1079 bp out of 1491 bp of nagE (GlcNAc permease).

2. pRE113-VAL-chitinΔloxP-Km$^R$D:

First round PCR was with primers VAL-BP-KO-F/VAL-Chitin-KO-MR and VAL-Chitin-KO-MF/VAL-Chitin-KO-R. The second PCR was with VAL-BP-KO-F/VAL-Chitin-KO-R as primers. The resulting construct inactivated and eliminated 10 genes (5 genes for (GlcNAc)$_2$ transport, GlcN kinase, β-endoglucosidase, exoI hexosaminidase, (GlcNAc)$_2$ phosphorylase and GlcNAc phosphomutase). The construct retained only the N-end 39 bp/1680 bp of BP and C-end 310 bp/1410 bp of phosphomutase with a 6 bp addition of XhoI site in the middle. A 1333 bp SalI ended kanamycin resistance gene within 2 loxP site was inserted into the XhoI site of the above construct.

3. pRE113-VAL-NagBΔloxP-Ery$^R$:

First round PCR was performed with primers VAL-NagB-KO-F/VAL-NagB-KO-MR and VAL-NagB-KO-MF/VAL-NagB-KO-R. The second round PCR was with primers VAL-NagB-KO-F/VAL-NagB-KO-R. In the final PCR construct, 383 bp (376-758) have been deleted out of 798 bp from the middle of NagB gene with a 6 bp XhoI site replacement. A 1137 bp SalI ended erythromycin resistance gene within 2 loxP sites was inserted into the XhoI site of the above construct.

4. pRE113-VAL-ChbΔloxP-Ery$^R$:

First round PCR was performed with primers VAL-Chb-KO-F/VAL-Chb-KO-MR and VAL-Chb-KO-MF/VAL-Chb-KO-R. The second round PCR was with primers VAL-Chb-KO-F/VAL-Chb-KO-R. The resulting construct inactivated and eliminated 7 genes of divergent chb operon (chitooligosaccharide deacetylase-COD, 3 genes for PTS type chitobiose transport system, annotated 6-phosphate-beta-glucosidase, annotated conserved hypothetical protein and chitobiose repressor). The construct retained only the C-end 359 bp/1281 bp of chitooligosaccharide deacetylase and C-end 389 bp/996 bp of chitobiose repressor with a 6 bp addition of XhoI site in the middle. A 1137 bp SalI ended erythromycin resistance gene within 2 loxP sites was inserted into the XhoI site of the above construct.

Genetic Properties

Vibrionacea mutants contained the following genetic markers as shown in FIGS. 8-11:

1. No marker knockout of Nag operon (permease, deacetylase and repressor).
2. Knockout NagB-deaminase with a loxP-Erythromycin resistance gene-loxP. The combined effect was to totally shut down the GlcNAc utilization system. This was proven by growth experiments in the presence of 20 mM GlcNAc, essentially no growth.
3. Knockout chitin operon which turned on the chitin utilization system with loxP-kanamycin resistance gene-loxP. The sensor, chiS, was not deleted, but since BP was deleted, chiS was permanently activated. It degraded chitin constitutively even in rich medium.
4. VAXB56 was derived from VAXB55 with the introduction of suicide plasmid pRE112-lac-Cre. pRE112-lac-Cre was created by inserting blunted AseI-EcoRI fragment from pCM157 plasmid (Marx et al. *Biotechniques* 33(5): 1062-1067 (2002)) into the SmaI site of pRE112 plasmid. The pRE112-lac-Cre plasmid expressed Cre enzyme in target cells and removed antibiotic marker enclosed by two loxP site leaving one loxP site instead. VAXB56 had the same properties as VAXB55 except the antibiotic markers were removed.
5. VAXB78 was derived from VAXB56 with additional chb operon deletion and antibiotic marker being removed. This knockout reduced the GlcN content in the final product and blocked the utilization of chitobiose (GlcN)$_2$ by the mutant.
6. Table 2 lists the phenotypic properties of the final strains.

TABLE 2

| Strain Name | Antibiotic Resistance | GlcNAc Utilization | Chitin Degradation System | Chitooligosaccharide deacetylase operon | Property |
|---|---|---|---|---|---|
| VAXB55 | Ampicillin, Kanamycin, Erythromycin | Negative | Turned On Constitutively | Positive | Accumulates GlcNAc and about 20% GlcN |
| VAXB56 | Ampicillin | Negative | Turned On Constitutively | Positive | Accumulates GlcNAc and about 20% GlcN |
| VAXB77 | Ampicillin, Erythromycin | Negative | Turned On Constitutively | Negative | GlcNAc:GlcN Ratio Equal to Original Chitin Source |
| VAXB78 | Ampicillin | Negative | Turned On Constitutively | Negative | GlcNAc:GlcN Ratio Equal to Original Chitin Source |

Results

Growth of the mutant was tested on colloidal chitin and finely ground seafood waste (lobster, crab, and shrimp shells). *V. alginolyticus* mutants were grown in rich medium (usually LB), or in minimal medium: 50% ASW (artificial sea water) buffered with 50 mM HEPES pH 7.5, 0.005% K$_2$HPO$_4$, 0.1% NH$_4$Cl and 0.5% DL-lactate as the carbon source. The cells tolerated NaCl, at least up to 5% in the medium. Good growth was evident in the range of room temperature to 42° C. The parental strain was naturally resistant to ampicillin, while the mutant, VAXB55 was also resistant to 50 µg/ml kanamycin and 75 µg/ml erythromycin, the genes having been introduced during genetic manipulation.

On agar plates the mutant strain swarmed very strongly, and spread even more extensively in a high salt medium, and at 37° C. than at room temperature. To isolate single colonies, an LB plate at 42° C. gave good results. In some cases, a MacConkey plate with 2% NaCl was used, although this method resulted in a greatly decreased cell number.

The 50 ml minimal medium (50% ASW/HEPES, pH 7.5/ K$^+$/NH4$^+$) with 1% DL-lactate, and either colloidal chitin or lobster waste as carbon source was inoculated with 200 µl LB overnight culture of wild type or VAXB55 mutant cells. The incubation was conducted at 37° C. At 0, 24 h, 48 h, 122 h, 144 h, 287 h time intervals, a 500 µl aliquot was centrifuged, and the supernatant was assayed for GlcNAc concentration by the Morgan-Elson method (Morgan and Elson Biochem. J. 28: 988 (1934)) with known concentrations of GlcNAc as standard. The result is shown in FIG. 12. The wild type strain, an active chitin and GlcNAc consumer, maintained a sub millimolar concentration of GlcNAc during the incubation. The target mutant, on the other hand, accumulated 11.6 mM (colloidal chitin) and 8.6 mM GlcNAc in the lobster waste culture. There was no GlcNAc positive utilization reversion or other mutations in VAXB55 during this long incubation period. Removal of GlcNAc from this static system ensured production of GlcNAc at minimal cost compared with the chemical methods.

The procedure is generally applicable to seafood waste, i.e., crab and shrimp waste products and gave the same results as obtained with lobster waste (FIGS. 13 and 14). Other sources of environmental chitin include fungal cell walls (Blumenthal and Roseman J. Bacteriol. 74: 222-224 (1957)).

In the second set of experiments, 200 µl overnight culture of VAXB56 in LB medium was inoculated into 50 ml minimal medium containing 100 µg/ml ampicillin, and 50% ASW/HEPES, pH 7.5/$K^+$/$NH_4^+$ with 1% DL-lactate. After incubation at 37° C. overnight, the cultures were then fed with excess colloidal chitin or lobster shell. At different time points, a 500 µl culture was withdrawn from the incubations, centrifuged, and the supernatants assayed for GlcNAc concentration by the Morgan-Elson method. The concentration of GlcNAc reached 8.6 mM at 24 hours for colloidal chitin or 10.2 mM at 55 hours for lobster waste. GlcN was also produced in these incubations. VAXB78 generated the exact percentage of GlcN depending on the original glucosamine content of the chitin source, while VAXB55 and VAXB56 generated an additional 20% more GlcN from the lobster waste because of activation of chb operon including the chitooligosaccharide deacetylase (COD).

In an additional experiment, a 2-liter jar fermentor was used (FIG. 14). At a constant pH of 7.0 and temperature of 37° C., with VAXB77 in LB rich medium and finely ground shrimp shell as the chitin source, the GlcNAc theoretical yield was attained and maintained at around 55 mM for 40 hours with only a residual GlcN content from the natural chitin.

Example 2

Degradation of Lobster and Shrimp Meal (Finely Ground Shells) Jar Fermentor Conditions are Listed for Both Lobster and Shrimp Shell Waste 1.1 Biomass
  Contents of lobster meal (total 2 L): 110 g (≈45 mM theoretical GlcNAc). HCl treatment to remove $Ca^{2+}$: 600 ml of 0.25 M HCl, 10 min×3 times, room temperature. Wash with water.
1.2 Cell Concentration
  LB medium
  $OD_{600}$ of strain VAXB77 in fermentor: 4.2
1.3 Fermentor Parameters
  Cultivation conditions: pH=7.0, 37° C.
  Total working volume: 2 L
Harvesting GlcNAc from the Fermentation
  The fermentation media contained many substances, as was expected. However, the following procedure gave essentially pure GlcNAc. The fermentation broths were centrifuged to remove all particulate matter, and transferred to an activated charcoal column as follows:
  200 g activated charcoal (Norit RO 0.8, pellet)
  500 ml products from shrimp shells (8.13 g/l) used for adsorption
  Column washed extensively with water
  50% ethanol used for desorption twice
  Flow rate: 2 ml/min
  Collect samples every 25 minutes
  Virtually all of the GlcNAc was adsorbed; the column was washed to remove other components of the medium with water, and eluted with 50% ethanol. (see FIGS. 15-18). The yields of highly purified GlcNAc from the raw material were better than 85-95%. The "theoretical GlcNAc" content of the waste products was determined by 2 methods: (a) The chitin content was assayed by standard methods, isolation from the raw material. (b) The glucosamine content of the waste was also assayed by standard methods (4 N HCl hydrolysis, 100° C., 16 hr, followed by drying, and Morgan-Elson method for glucosamine). The two methods gave excellent agreement.

Example 3

Conversion of N-Acetylglucosamine to Glucosamine

GlcNAc hydrolysis proceeds quantitatively in 0.1 N HCl at 100° C. for 2 hr. Spray drying or concentrating the solution removes excess HCl and the acetic acid, giving GlcN.HCl.

Example 4

Ethanol Production from Degradation Products of Chitin Wastes by *S. cerevisiae* (Mutant S9)

Medium YL3 for Growing *S. cerevisiae* (Mutant S9)

| | |
|---|---|
| Yeast extract | 5 g/l |
| $KH_2PO_4$ | 3 g/l |
| $Na_2HPO_4$ | 4.5 g/l |
| $(NH_4)_2SO_4$ | 2 g/l |
| $MgSO_4 \cdot 7H_2O$ | 0.5 g/l |
| Methionine | 20 mg/l |

Cultivation Conditions
  Batch cultivation mode;
  Working volume: 9 ml
  Initial pH: 6.0
  Anaerobic, 30° C., 200 rpm
  Initial inoculum density: $OD_{600}$=0.04
  Total cultivation time: 4 days

TABLE 3

Ethanol production from environmental chitin

| Cultivation system | Ethanol (mM) | Ethanol (mol/mol GlcNAc) |
|---|---|---|
| Only Medium YL3 | 0.10 | — |
| Shrimp shell degradation product (≈8 g/l GlcNAc) | 0.05 | — |
| Shrimp shell degradation product + Medium YL3 | 3.03 | 0.82 |
| Lobster meal degradation product (≈6 g/l GlcNAc) | 0.02 | — |

TABLE 3-continued

Ethanol production from environmental chitin

| Cultivation system | Ethanol (mM) | Ethanol (mol/mol GlcNAc) |
|---|---|---|
| Lobster meal degradation product + Medium YL3 | 1.89 | 0.83 |

TABLE 4

Ethanol production by the yeast mutant *S. cerevisiae* (mutant S9) from GlcNAc and Glucose

| | mmol/liter culture | mg/liter culture |
|---|---|---|
| GlcNAc-limited oxygen | 21.5 | 990 |
| GlcNAc-aerobic | 21.1 | 969 |
| Glucose-limited oxygen | 22.5 | 1036 |
| Glucose-aerobic | 22.0 | 1013 |

Example 5

Co-Fermentation of *V. alginolyticus* (Mutant 77) and *S. cerevisiae* (Engineered Yeast S9)

| | |
|---|---|
| Colloidal chitin | 10 g |
| Yeast extract | 5 g/l |
| $KH_2PO_4$ | 3 g/l |
| $Na_2HPO_4$ | 4.5 g/l |
| $(NH_4)_2SO_4$ | 2 g/l |
| $MgSO_4 \cdot 7H_2O$ | 0.5 g/l |
| Methionine | 20 mg/l |

Batch cultivation mode;
Working volume: 5 ml
pH 6.5
Aerobic, 30° C., 200 rpm
Initial separate inoculum density of two strains: $OD_{600}$=0.04
Total cultivation time: 5 days
As shown in FIG. 19, co-culture effectively produced ethanol from chitin waste.

What is claimed is:

1. A genetically engineered mutant bacterium of the genus Vibrionaceae wherein the following genes are deleted by homologous recombination:
   a) nagA,
   b) nagB,
   c) nagC,
   d) nagE, and
   e) the genes of the chitin operon excluding the genes which encode a chitin catabolic sensor (chiS).

2. The genetically engineered mutant bacterium of claim 1, wherein the genes of a chitobiose operon are deleted via homologous recombination.

3. The genetically engineered mutant bacterium according to claim 1, wherein the mutant is capable of releasing N-acetylglucosamine into a growth medium containing chitin.

4. The mutant bacterium according to claim 1, wherein the genes deleted in the chitin operon include a gene encoding a periplasmic $(GlcNAc)_2$ binding protein (BP).

5. The genetically engineered mutant bacterium according to claim 1, wherein said mutant bacterium is a mutant of a *Vibrio* species.

6. The genetically engineered mutant bacterium according to claim 1, wherein said mutant bacterium is a mutant of *Vibrio alginolyticus*, *Vibrio cholerae* or *Vibrio furnissii*.

7. A method of using the genetically engineered mutant bacterium according to claim 1, to obtain at least one of N-acetylglucosamine and glucosamine, comprising:
   (a) adding the genetically engineered mutant bacterium to an extracellular medium comprising chitin;
   (b) converting the chitin into products comprising N-acetylglucosamine by means of the genetically engineered mutant bacterium; and
   (c) obtaining at least one of N-acetylglucosamine and glucosamine in the extracellular medium.

8. The method according to claim 7, wherein the N-acetylglucosamine can be purified from the extracellular medium by means of an activated charcoal column.

9. The method according to claim 7, wherein the chitin is environmental chitin obtained from a source selected from the group consisting of algae, fungi and invertebrates.

10. The method according to claim 9, wherein the invertebrate chitin is obtained from a source selected from the group consisting of arthropod cuticles, annelida, and mollusca, or where the fungal chitin is obtained from fungal cell walls.

11. The method according to claim 7, further comprising converting N-acetylglucosamine to glucosamine by acid hydrolysis or by means of a deacetylase.

12. A method for forming a genetically engineered mutant bacterium of the genus Vibrionaceae according to claim 1, comprising:
   (a) obtaining a bacterium of the genus Vibrionaceae from a source;
   (b) deleting the following genes by homologous recombination: nagA, nagB, nagC, nagE, and the genes of the chitin operon excluding the genes which encode a chitin catabolic sensor (chiS); and
   (c) forming the genetically engineered mutant bacterium.

13. The method according to claim 12, wherein the method further comprises deleting the genes of a chitobiose operon via homologous recombination.

14. The method according to claim 12, wherein the genetically engineered mutant bacterium is a genetically engineered mutant of a *Vibrio* species selected from the group consisting of *Vibrio alginolyticus*, *Vibrio cholerae*, and *Vibrio furnissii*.

15. A method for using the genetically engineered mutant bacterium according to claim 1, to make ethanol comprising:
   (a) adding the genetically engineered mutant bacterium to a medium comprising chitin;
   (b) converting the chitin into a degradation product comprising N-acetylglucosamine by means of the genetically engineered bacterium; and
   (c) converting the N-acetylglucosamine into ethanol using genetically engineered yeast cells.

16. The method of claim 15, wherein step (b) further comprises harvesting the extracellular N-acetylglucosamine for adding to a separate culture of genetically engineered yeast cells and allowing the yeast to convert the N-acetylglucosamine into ethanol.

17. The method according to claim 15 wherein in step (c) the conversion occurs via co-cultivating a mixture of genetically engineered yeast cells in the medium containing the genetically engineered mutant bacterium and extracellular N-acetylglucosamine.

18. The method according to claim 15, wherein step (a) further comprises adding a mixture of genetically engineered yeast cells to the mutant bacterium in the medium to create a co-culture of genetically engineered mutant bacterium and genetically engineered yeast cells.

19. The method according to claim 15, wherein the genetically engineered mutant bacterium is of the species *Vibrio alginolyticus*.

20. The method according to claim 15, wherein the genetically engineered yeast is of the genus *Saccharomyces*.

\* \* \* \* \*